US007435284B2

(12) United States Patent
Piccinini et al.

(10) Patent No.: US 7,435,284 B2
(45) Date of Patent: Oct. 14, 2008

(54) PARALLEL-PLATE DIFFUSION GAS DEHUMIDIFIER AND METHODS FOR USE

(75) Inventors: James Domenick Piccinini, Delmar, NY (US); Lauren R. Basch, East Greenbush, NY (US); Adam Bailey, Albany, NY (US)

(73) Assignee: Thermo Electron Corporation, East Greenbush, NY (US)

( * ) Notice: Subject to any disclaimer, the term of this patent is extended or adjusted under 35 U.S.C. 154(b) by 190 days.

(21) Appl. No.: 11/281,273

(22) Filed: Nov. 17, 2005

(65) Prior Publication Data

US 2007/0107594 A1 May 17, 2007

(51) Int. Cl.
*B01D 53/22* (2006.01)

(52) U.S. Cl. .......................... 95/52; 95/45; 96/4; 96/7; 96/11; 96/12; 96/14

(58) Field of Classification Search .................... 95/45, 95/52; 96/4, 7, 10, 11, 12, 14; 73/28.01, 73/31.07, 863.21
See application file for complete search history.

(56) References Cited

U.S. PATENT DOCUMENTS

| | | | | |
|---|---|---|---|---|
| 3,604,246 A | | 9/1971 | Toren | 73/38 |
| 3,735,559 A | | 5/1973 | Salemme | 55/16 |
| 4,341,538 A | * | 7/1982 | Vadnay et al. | 96/6 |
| 5,084,073 A | * | 1/1992 | Prasad | 95/52 |
| 5,108,464 A | | 4/1992 | Friesen et al. | |
| 5,571,945 A | | 11/1996 | Koutrakis et al. | 73/28.03 |
| 5,637,809 A | | 6/1997 | Traina et al. | 73/864.12 |
| 5,693,122 A | * | 12/1997 | Berndt | 96/7 |
| 5,824,919 A | | 10/1998 | Hansen | |
| 5,827,429 A | * | 10/1998 | Ruschke et al. | 96/7 |
| 5,932,795 A | | 8/1999 | Koutrakis et al. | 73/28.01 |
| 6,087,029 A | | 7/2000 | Golovin et al. | |
| 6,151,953 A | | 11/2000 | Patashnick et al. | 73/28.01 |

(Continued)

FOREIGN PATENT DOCUMENTS

GB 0 308 988 A * 7/1997

(Continued)

OTHER PUBLICATIONS

International Search Report for corresponding PCT Application PCT/US2006/043522 mailed May 16, 2007.

(Continued)

*Primary Examiner*—Jason M Greene
(74) *Attorney, Agent, or Firm*—Heslin Rothenberg Farley & Mesiti P.C.

(57) ABSTRACT

A parallel-plate diffusion gas dehumidifier has a treatment zone having at least one water-permeable membrane. The gas dehumidifier includes an untreated gas inlet, a treatment zone bounded by water-permeable membranes, a support structure for the membranes, access to a source of vacuum, and a dehumidified gas outlet. The cross section of the treatment zone may be provided in various shapes, for example, rectangular. The gas dehumidifier inlet and outlet include flow transitions that minimize the obstruction of particles passing through the dehumidifier. The dehumidifier may be used in particle sampling systems to dehumidify the sample gas prior to introducing the sample gas to a mass measuring device and mass flow controller. Methods of operating the gas dehumidifier and the particle sampling system are also provided.

44 Claims, 11 Drawing Sheets

U.S. PATENT DOCUMENTS

| | | | | |
|---|---|---|---|---|
| 6,171,374 | B1 * | 1/2001 | Barton et al. | 95/52 |
| 6,413,298 | B1 * | 7/2002 | Wnek et al. | 95/52 |
| 6,455,859 | B1 | 9/2002 | Orr et al. | 250/379 |
| 6,485,545 | B1 | 11/2002 | Ohlrogge et al. | 96/4 |
| 6,505,523 | B1 | 1/2003 | Taylor et al. | 73/863.01 |
| 6,651,480 | B2 | 11/2003 | Patashnick et al. | 73/1.34 |
| 6,755,399 | B2 * | 6/2004 | Shimanuki et al. | 95/52 |
| 2003/0010205 | A1 | 1/2003 | Bikson et al. | 95/52 |
| 2003/0049854 | A1 | 3/2003 | Rhodes | 436/106 |
| 2005/0072303 | A1 | 4/2005 | Weidenmann | |
| 2006/0021615 | A1 * | 2/2006 | Kertzman | 128/201.13 |

FOREIGN PATENT DOCUMENTS

| | | | |
|---|---|---|---|
| WO | 0066305 | A | 12/1999 |

OTHER PUBLICATIONS http://www.permapure.com/OurTechnology.htm, "Our Technology," Perma Pure LLC, Toms River, New Jersey, May 27, 2005 (2 pages).

http://www.permapure.com/Products/PD-Series/PD.htm, "PD-Series Gas Dryers," Perma Pure LLC, Toms River, New Jersey, May 16, 2005 (2 pages).

http://www.permapure.com/Products/MD-Series/MD.htm, "MD-Series Gas Dryers," Perma Pure LLC, Toms River, New Jersey, May 16, 2005 (2 pages).

"PD™-Series Dryers—Operation & Installation Manual," Perma Pure Inc., Toms River, New Jersey, Form #204 (3 pages).

"MD™-Series Gas Dryer—Installation & Operation Manual," Perma Pure LLC, Toms River, New Jersey, Form #203 (2 pages).

"DuPont™—Nafion® PFSA Membranes, N-112, NE-1135, N-115, N-117, NE-1110—perfluorosulfonic acid polymer—Product Information," DuPont Fluoroproducts, Nafion® Global Customer Service, Fayetteville, North Carolina, NAE 101 (Feb. 2004) (4 pages).

http://www.permapure.com/Our Technology.htm, "Our Technology," Perma Pure LLC, Toms River, New Jersey, May 27, 2005 (2 pages).

http://www.permapure.com/Products/MD-Series/MD.htm, "MD-Series Gas Dryers," Perma Pure LLC, Toms River, New Jersey, May 16, 2005 (2 pages).

"DuPont™—Nafion®PFSA Membranes, N-112, NE-1135, N-115, N-117, NE-1110—perfluorosulfonic acid polymer—Product Information," DuPont Fluoroproducts, Nafion® Global Customer Service, Fayetteville, North Carolina, NAE 101 (Feb. 2004) (4 pages).

* cited by examiner

PARALLEL-PLATE DIFFUSION GAS DEHUMIDIFIER AND METHODS FOR USE

TECHNICAL FIELD

This invention relates generally to gas samplers, and more particularly to methods and devices for dehumidifying gas streams introduced to an apparatus for collecting and detecting particulate in a gas sample.

BACKGROUND OF THE INVENTION

Air borne particulate, either occurring naturally, such as pollen and dust, or generated through industry, such as smoke or automobile exhaust, can be hazardous to human health. Particulate concentration and content may typically be monitored to, among other things, evaluate the changes in particulate matter due to natural or industrial activity. Particulate sampling systems are typically used to collect and categorize the particulate content of ambient air. One typical particulate sampling system is provided by the Environmental Instruments Division of Thermo Electron Corporation of East Greenbush, N.Y. and described in U.S. Pat. No. 6,502,450, the disclosure of which is incorporated by reference herein in its entirety. The particulate sampled by such systems is typically characterized by the size of the particles collected, for example, particulate matter (PM) having diameters less than or equal to 10 microns (μm), that is, particles designated "$PM_{10}$" or "PM10" particles in the art, or lower may be collected.

When sampling gas using a particulate sampling system it is often desirable to remove as much water vapor as possible from a sampled gas stream before measuring the particulate content, for example, measuring the mass of the particulate. The presence of water vapor in a sampled gas stream can interfere with the accurate measurement of, for example, the mass of particulate matter in the gas stream. The effect of the presence of water vapor upon the measuring device can be particularly acute when the measuring device is operated at temperatures at which water vapor tends to condense on the sensing hardware, for example, at temperatures of about 30 degrees C. or lower. Aspects of the present invention are adapted to remove water vapor from sample gas streams whereby the particulate measuring device can provide a more accurate indication of the particulate content of the sampled gas stream.

In addition, while removing water vapor from the gas stream, it is important that the water vapor removal device or method minimize or avoid undesirable impact upon the particulate matter in the sample stream. For example, conventional water vapor removal devices, that is, "dehumidifiers" or "dryers" designed to remove water vapor from a gas stream, for example, those disclosed in U.S. Pat. Nos. 6,651,480; 6,151,953; 6,171,374; 5,932,795; 5,571,945; and 3,735,559, may typically interfere with the goal of the particulate sampling system, that is, collecting particles. Among other things, conventional dehumidifiers, for example, bundled-tube dehumidifiers, typically provide at least some obstruction to the flow of gas whereby particles are either hindered or captured in the dehumidifier.

Thus, a need exists for dehumidifying devices and methods that effectively remove water vapor from a sample gas stream while minimizing the impact of the devices and methods on the flow of particles in the gas stream. Aspects of the present invention provide some means of effecting the desired dehumidification while minimizing the impact upon the particle content of the gas stream.

SUMMARY OF THE INVENTION

The present invention was conceived and developed to overcome the above-mentioned limitations of existing methods and devices for dehumidifying gas streams, in particular, the limitations of existing methods and devices for dehumidifying gas streams used in conjunction with particulate sampling systems.

One aspect of the invention is a membrane diffusion gas dehumidifier having an inlet for a gas having a first moisture content; a treatment zone comprising a flow path having a first boundary, a second boundary opposite the first boundary, and a width comprising the distance between the first boundary and the second boundary, wherein at least one of the first boundary and the second boundary of the flow path comprises a water-permeable membrane, the membrane having a first side exposed to the treatment zone and a second side opposite the first side; a transitional flow path between the inlet and the treatment zone; means for exposing the second side of the membrane to a treatment gas having a second moisture content, lower than the first moisture content; and a dehumidified gas outlet. In one aspect, the dehumidifier includes at least one support structure adapted to support the membrane. In another aspect, the treatment zone flow path comprises a rectangular cross section in the direction of flow.

Another aspect of the invention is a method of dehumidifying a gas stream, the method including providing a diffusion gas dehumidifier having a gas inlet; a treatment zone comprising a flow path having a first boundary, a second boundary opposite the first boundary, and a width comprising the distance between the first boundary and the second boundary, wherein at least one of the first boundary and the second boundary of the flow path comprises a water-permeable membrane, the membrane having a first side exposed to the treatment zone and a second side opposite the first side; a transitional flow path between the gas inlet and the treatment zone; and an outlet; introducing an untreated gas stream having a first water vapor content to the gas inlet; passing the untreated gas stream from the gas inlet through the transitional flow path to the treatment zone; passing the untreated gas stream through the treatment zone; passing a treatment gas stream passed the second side of the membrane, the treatment gas stream having a second water vapor content less than the first water vapor content, whereby at least some water vapor in the untreated gas stream passes through the membrane to the treatment gas stream to provide a dehumidified gas stream; and discharging the dehumidified gas stream from the outlet. In one aspect, the untreated gas stream introduced to the inlet includes at least some particulate matter, and wherein the method is practiced wherein the dehumidified gas stream discharged from the outlet includes most of the particulate matter introduced at the inlet. In another aspect, passing a treatment gas stream passed the second side of the membrane may comprise passing the treatment gas stream as a turbulent flow whereby the formation of a boundary layer on the second side of the membrane is minimized.

Another aspect of the invention is a particulate matter sampling system for a gas, the system including a diffusion gas dehumidifier having a gas inlet; a treatment zone comprising a flow path having a first boundary, a second boundary opposite the first boundary, and a width comprising the distance between the first boundary and the second boundary, wherein at least one of the first boundary and the second boundary of the flow path comprises a water-permeable membrane, the membrane having a first side exposed to the treatment zone and a second side opposite the first side; at least one vacuum inlet; a least one vacuum outlet; and a dehumidified gas outlet; a particulate matter measuring device having an inlet in fluid communication with the dehumidifier gas outlet and an outlet; a flow controller having an inlet in fluid communication with the particulate matter measuring device outlet and an outlet in fluid communication with the at least one dehumidifier vacuum inlet; and a source of vacuum operatively connected to the at least one dehumidifier vacuum outlet.

A further aspect of the invention is a method of treating a gas stream, the method including providing a dehumidifying device having water vapor permeable membrane, the membrane having a sample side and a purge side opposite the sample side; passing the gas stream having a first water vapor concentration passed the sample side of the membrane; turbulently passing a treatment gas stream having a second water vapor concentration lower than the first water vapor concentration passed the purge side of the membrane; passing at least some water vapor from the gas stream through the membrane to produce a dehumidified gas stream having a third water vapor concentration lower than the first water vapor concentration; and returning the dehumidified gas stream as the treatment gas stream in the dehumidifying device. In one aspect, the method further includes expanding the dehumidified gas stream to produce an expanded and dehumidified gas stream having a fourth water vapor concentration, lower than the third water vapor concentration.

A still further aspect of the invention is a membrane support structure adapted to provide at least one flow passage for transmitting a treatment fluid past the membrane, the support structure including a plate having a surface; and a plurality of ribs mounted to the plate, the plurality of ribs adapted to support the membrane; wherein when the membrane is mounted to the support structure, the membrane, the plurality of ribs, and the surface of the plate define the boundaries of the at least one flow passage. In one aspect, the at least one flow passage comprises a cross section sized to maximize either treatment fluid flow velocity or treatment fluid flow turbulence for a given treatment fluid flow rate, for example, to minimize the development of a boundary layer on the membrane.

These and other aspects, features, and advantages of this invention will become apparent from the following detailed description of the various aspects of the invention taken in conjunction with the accompanying drawings.

BRIEF DESCRIPTION OF THE DRAWINGS

The subject matter, which is regarded as the invention is particularly pointed out and distinctly claimed in the claims at the conclusion of the specification. The foregoing and other objects, features, and advantages of the invention will be readily understood from the following detailed description of aspects of the invention taken in conjunction with the accompanying drawings in which:

DETAILED DESCRIPTION OF THE INVENTION

Figure 1:
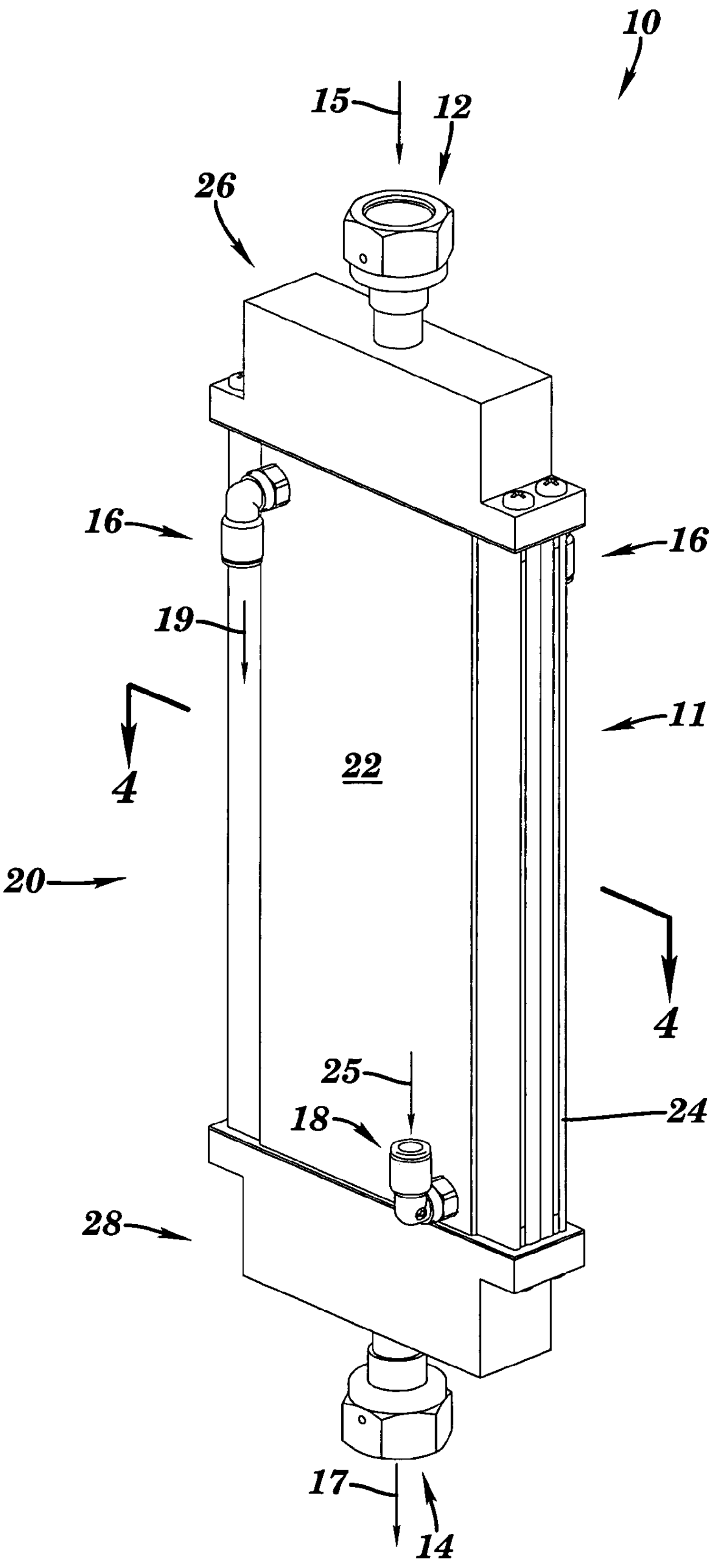
FIG. 1 is a perspective view of a parallel plate gas dehumidifier according to one aspect of the invention.

Aspects of the present invention provide methods and devices for removing water vapor from particulate-containing gas streams while minimizing the impact of the water vapor removal upon the particulate content of the gas stream. FIG. 1 is a perspective view of a parallel plate gas dehumidifier or dryer 10 according to one aspect of the invention. Dehumidifier 10 includes a housing 11, an untreated gas inlet 12, a treated gas outlet 14, one or more treatment gas outlets 16, and one or more treatment gas inlets 18. According to one aspect of the invention, untreated gas, indicated by arrow 15, having at least some water vapor, is introduced to gas inlet 12, passes through and is dehumidified in dehumidifier 10, and then the treated gas, indicated by arrow 17, is discharged from gas outlet 14. At the same time, a source of treatment gas, for example, a gas having less water vapor and/or less vapor pressure and/or less pressure than the gas 15 introduced to inlet 12, is introduced to treatment gas inlets 18, as indicated by arrow 19. The gas introduced to inlets 18 may be introduced by means of sub-atmospheric pressure or vacuum applied to outlets 16. The vacuum introduced to outlet 16 may introduce a vacuum to dehumidifier 10 and may draw a flow of gas into inlet 18, as indicated by arrow 25. According to aspects of the invention, the treated gas 17 discharged from gas outlet 14 typically will contain less water vapor than the untreated gas 15 introduced to inlet 12. The treated or dehumidified gas stream 17 exiting outlet 14 may be forwarded to further treatment or analysis, for example, to a mass detector or collector, as will be discussed below.

Figure 2:
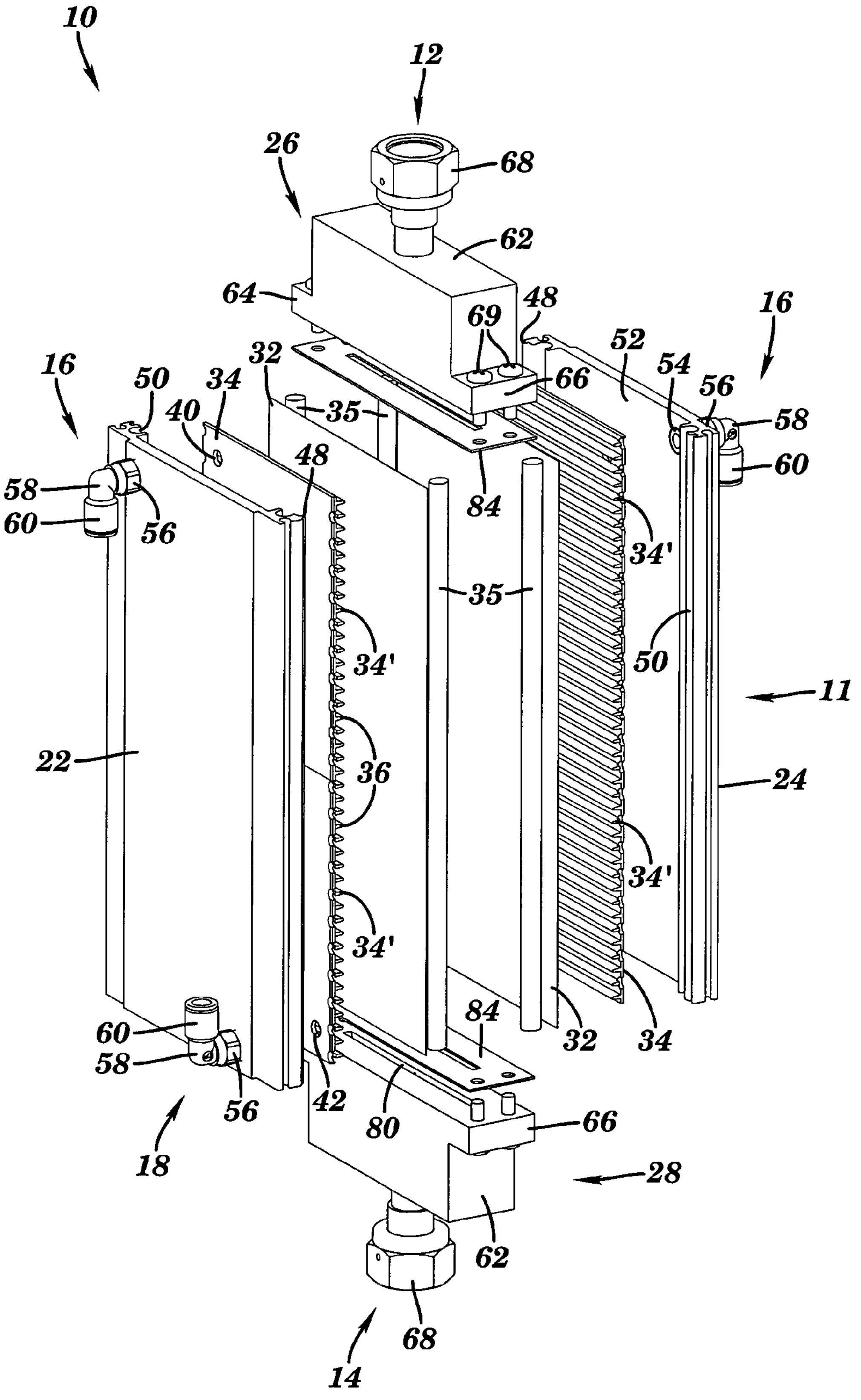
FIG. 2 is an exploded perspective view of the dehumidifier shown in FIG. 1.
Figure 3:
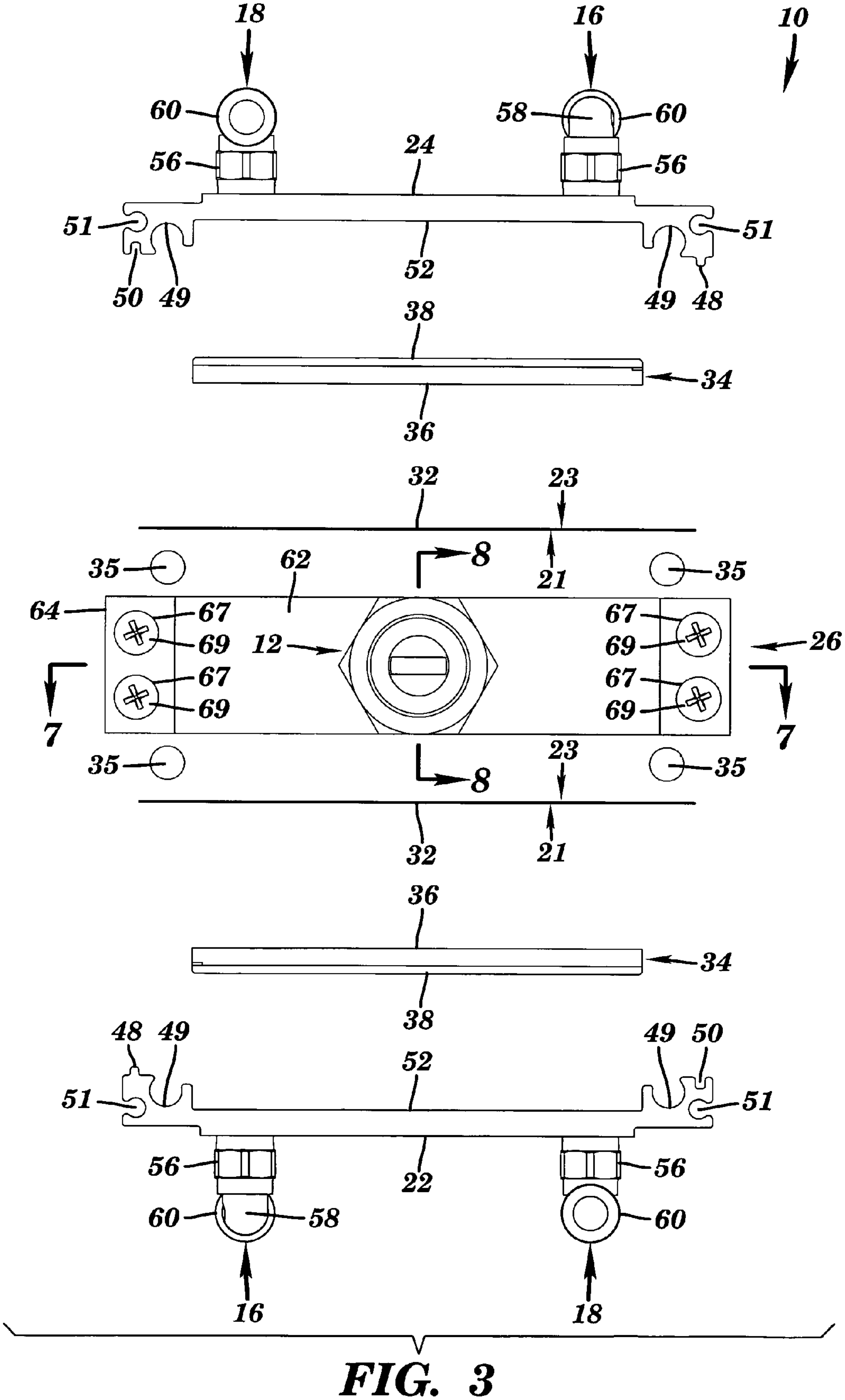
FIG. 3 is an exploded plan view of the dehumidifier shown in FIG. 1.
Figure 4:
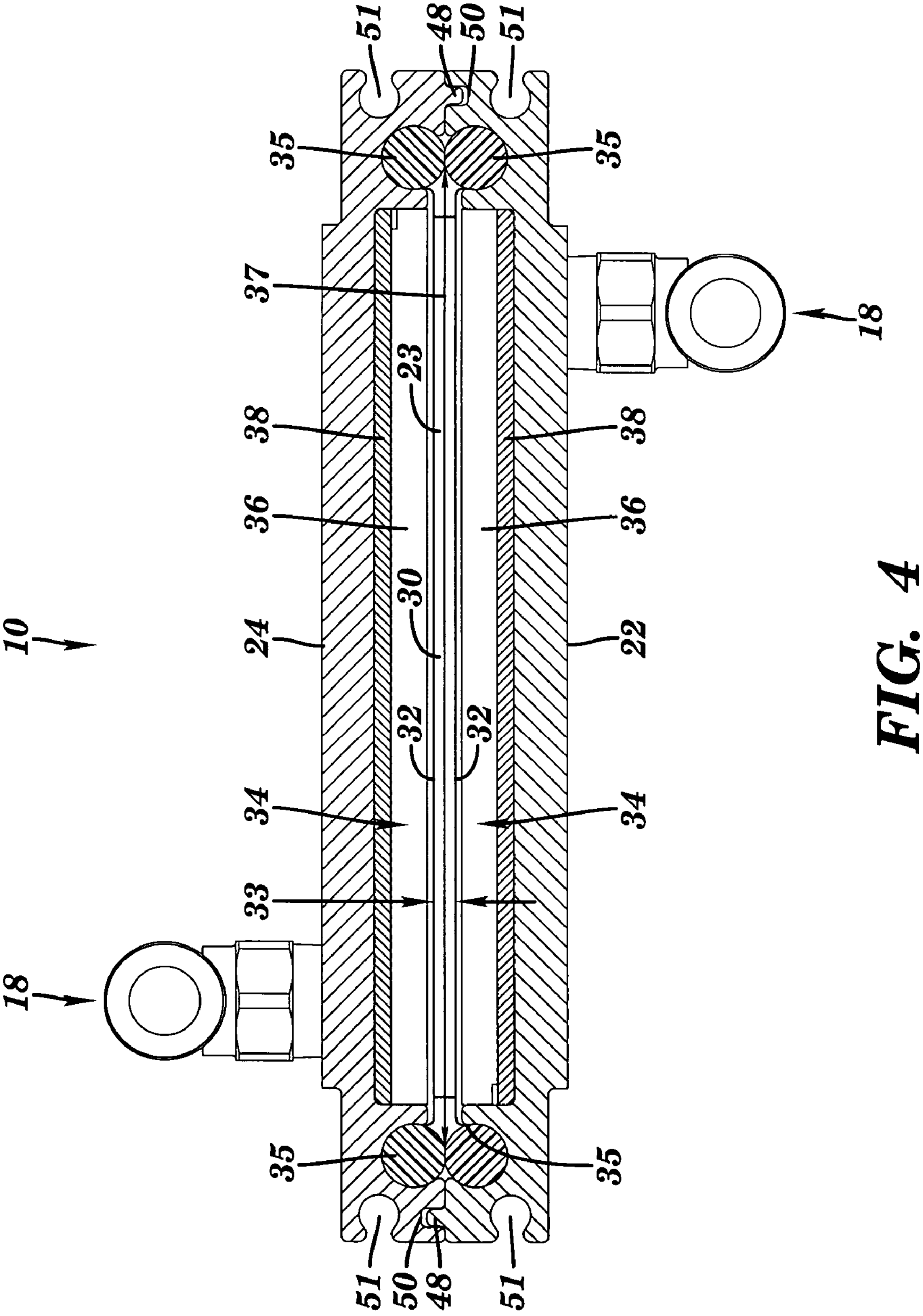
FIG. 4 is a cross sectional view of the dehumidifier shown in FIG. 1 as viewed along section lines 4-4 in FIG. 1.

FIG. 2 is an exploded perspective view of dehumidifier 10 and FIG. 3 is an exploded plan view of dehumidifier 10 shown in FIG. 1. As shown in FIGS. 2 and 3, housing 11 includes an outer shell 20 comprising two side plates 22 and 24 and two end caps 26 and 28. FIG. 4 is a cross sectional view of dehumidifier 10 as viewed along section lines 4-4 in FIG. 1.

As shown most clearly in the cross sectional view of FIG. 4, according to one aspect of the present invention, humidifier 10 includes at least one longitudinal passage or treatment zone 30 bounded by at least one water-vapor-permeable membrane 32, for example, at least two water-permeable membranes 32. Treatment zone 30 may typically have a separation distance or treatment zone width 33 between the boundaries, (for example, the boundaries defined by membranes 32) and an effective treatment zone length 37. Separation distance 33 may range from about 0.010 inches to about 1.0 inch, and is typically between about 0.075 inches and about 0.175 inches. Treatment zone length 37 may range from about 2 inches to about 36 inches, and is typically between about 1 inch and about 6 inches, for example, about 3.25 inches. The rectangular cross section of the flow path defined by width 33 and length 37 may have an aspect ratio (length/width) of at least about 5 to 1, for example, at least about 10 to 1, or even about 20 to 1, or larger.

Figure 12A:
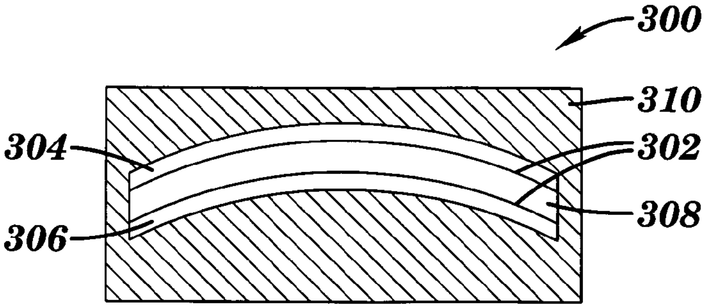
FIGS. 12A, 12B, and 12C are schematic views of further flow path cross sections according to further aspects of the invention.
Figure 12B:
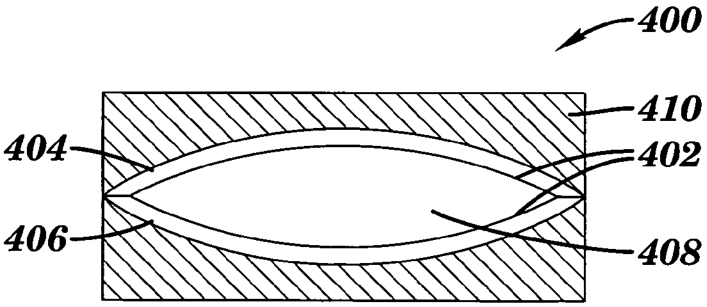
Figure 12C:
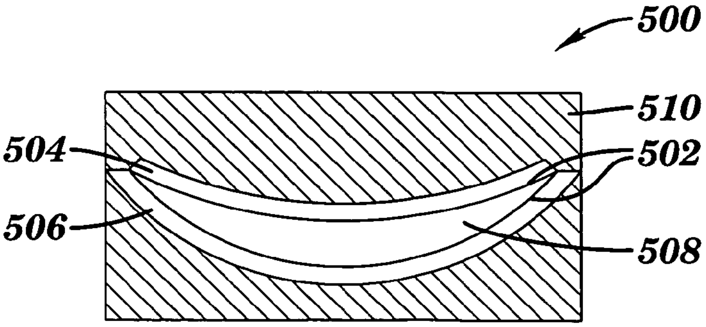

In the aspect of the invention shown in FIG. 4, the flow path between the boundaries of the flow passage is generally rectangular in cross section; however, the invention is not limited to a rectangular cross section. According to aspects of the invention, the flow path may have many diverse geometric shapes, including annular passages; sections of annular passages; arch-shapes, for example, crescent shapes, and cat's eye shapes; angled passages, for example, bent rectangles (as in the shape of the a section or corner of rectangular cylinder). Some typical cross sections of flow paths according to aspects of the invention are shown in FIGS. 12A, 12B, and 12C, discussed below. In one aspect of the invention, the flow path comprises a first boundary and a second boundary opposite the first boundary and a width comprising the distance between the first boundary and the second boundary. For example, where at least one of the first boundary and the second boundary of the flow path comprises a water-permeable membrane. Although the following discussion will describe aspects of the invention having a generally rectangular flow path, it is to be understood that many flow path geometries are included within the scope of the invention.

According to aspects of the invention, a "water-permeable membrane" may mean that the membrane has the property of being able to transfer at least some water or water vapor from one side of the membrane to another side of the membrane, for example, while preventing the passage of at least one other material through the membrane. The transfer or passage of water or water vapor may be effected by various gas or liquid transfer processes, including one or more of diffusion, osmosis, permeation, sorption, and adsorption, among others. In one aspect of the invention, the transfer of water and/or water vapor may be practiced by means of pervaporation.

According to one aspect of the invention, while a gas containing at least some water vapor passes through passage 30 at least some of the water vapor passes, for example, diffuses, through at least one membrane 32 whereby at least some water vapor is removed from the gas stream. According to one aspect of the invention, membrane 32 may comprise any membrane adapted to pass water vapor, for example, due to a water vapor concentration gradient across membrane 32. However, membrane 32 may comprise a perfluorosulfonic acid (PFSA) polymer, for example, a Nafion® PFSA polymer provided by DuPont Fluoroproducts of Fayetteville, N.C. and described in DuPont Product Information sheet NAE101 (February 2004), the disclosure of which is incorporated by reference herein, or its equivalent. Membrane 32 may vary in thickness from about 0.001 inches (24.4 microns) to about 0.050 inches (1270 microns), but may typically have a thickness of between about 0.005 inches (127 microns) to about 0.010 inches (244 microns).

The thickness of membrane 32 may affect the performance of humidifier 10. Specifically, analysis has shown that there may be an interrelationship between water removal efficiency and the durability of membrane 32. Membrane 32 and any other membrane disclosed herein may comprise a Nafion N-112 PFSA polymer having a nominal thickness of about 0.002 inches (51 microns), or its equivalent, that provides acceptable water removal efficiency while providing improved membrane durability. Other types and thicknesses of membranes may be used depending upon the size, loading, and desired service life of dehumidifier 10.

In one aspect of the invention, membrane 32 may be supported by a membrane support structure 34, for example, to support membrane 32 under the load imposed by a pressure drop across membrane 32, for instance, due to applied vacuum. Membrane support structure 34 provides a support structure that, among other things, prevents membrane 32 from collapsing and blocking the gas flow paths 41 (see below). Contact between support structure 34 and membrane 32 may be minimized to limit the reduction in the effective area of membrane 32 due to contact with support structure 34. Any support structure 34 may be provided that is adapted to provide sufficient support for membrane 32 while minimizing the obstruction of flow through membrane 32, for example, by providing sufficient open area not directly in contact with membrane 32. As shown in FIG. 2, humidifier 10 may include one or more membrane support structures 34 having a plurality of support ribs 36 adapted to support membrane 32, for example, a plurality of transversely mounted support ribs. The design and spacing of ribs 36 minimizes damage to membrane 32, for example, prevents puncturing membrane 32, and minimizes sagging of membrane 32, for example, due to the vacuum applied to the opposite side or the "purge side" of membrane 32.

Figure 5:
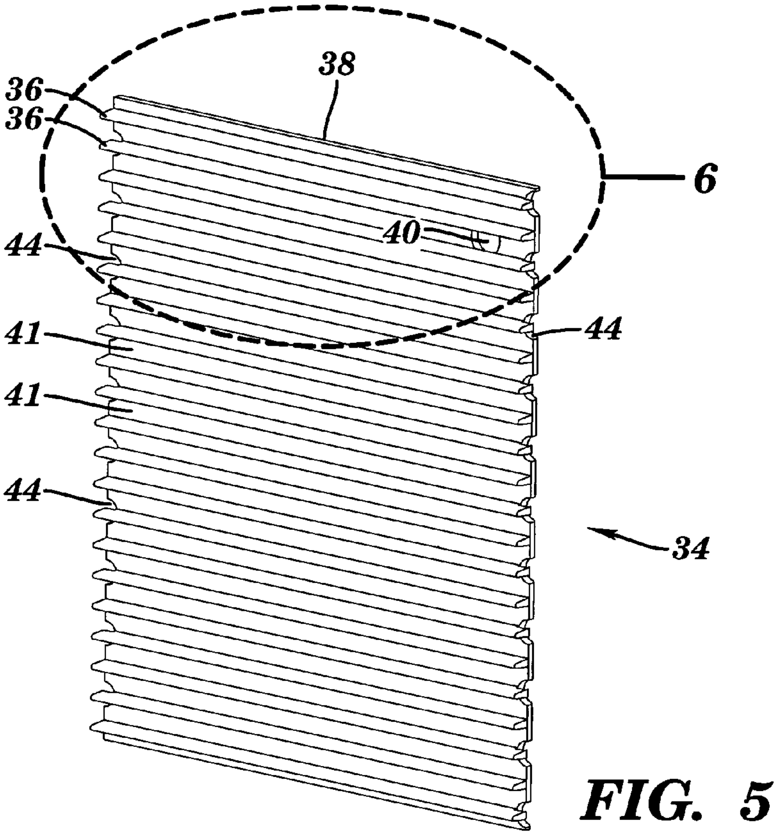
FIG. 5 is a perspective view of a membrane support structure according to one aspect of the invention.
Figure 6:
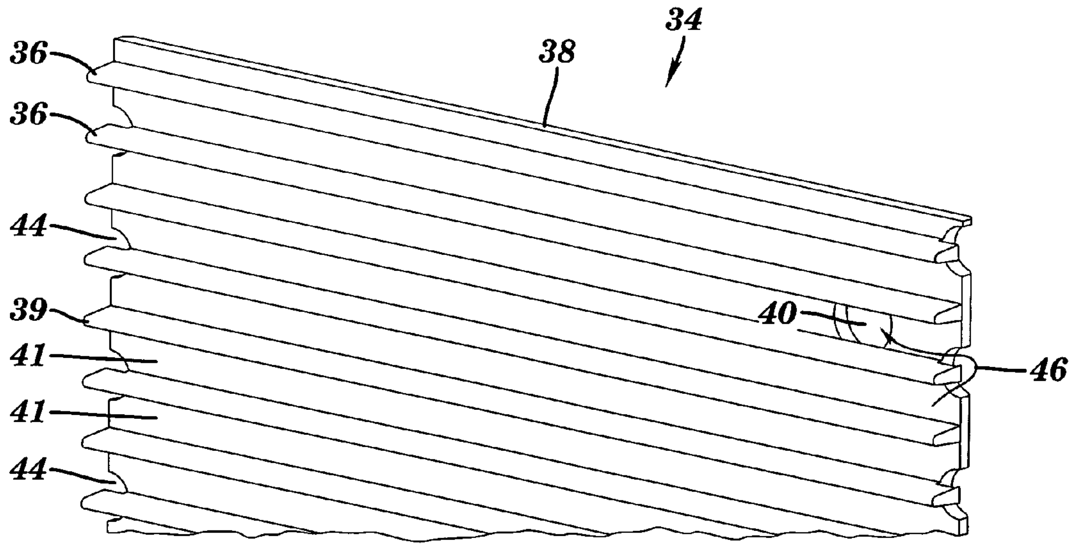
FIG. 6 is a detailed view of the support structure shown in FIG. 5 as indicated by detail 6 in FIG. 5.

FIG. 5 is a perspective view of one membrane support structure 34 according to one aspect of the invention. FIG. 6 is a detailed view of the support structure 34 shown in FIG. 5 as identified by detail 6 in FIG. 5. As shown in FIGS. 5 and 6, membrane support structure 34 may comprise a substantially flat plate 38 upon which ribs 36 are mounted. As shown in FIG. 5, according to one aspect of the invention, ribs 36 may comprise a plurality of parallel structures extended transversely or laterally across plate 38. In another aspect of the invention, ribs 36 may extend longitudinally, for example, substantially perpendicular to the direction of ribs 36 shown in FIGS. 5 and 6. In another aspect of the invention, ribs 36 may extend both longitudinally and laterally, or at an angle oblique to the longitudinal or lateral axes of support structure 34. Ribs 36 may comprise any convenient cross-sectional shape, for example, rectangular, triangular, square, semicircular, and the like. In the aspect of the invention, shown in FIGS. 5 and 6, the cross section of ribs 36 may comprise a substantially triangular shape with a rounded apex 39, for example, to minimize or prevent damage to membrane 32.

According to another aspect of the invention, support structure 34 may also provide a pathway through which a vacuum passes through dehumidifier 10 and contacts membrane 32. Ribs 36 and membrane 32 (not shown in FIGS. 5 and 6) may define passageways 41 through which a vacuum source may be transmitted along support structure 34. Support structure plate 38 may include a plurality of holes 40 and 42 through plate 38 which allow fluid communication between passageways 41 and a source of vacuum. A source of vacuum may be introduced to hole 40 and the flow of vacuum may flow from hole 42 to hole 40, that is, in a direction counter-current to the flow of untreated gas through humidifier 10. In another aspect of the invention, a source of vacuum may be introduced to hole 42 and the flow of vacuum may flow from hole 40 to hole 42, that is, in a direction co-current to the flow of untreated gas through humidifier 10. For example, as shown in FIG. 2, hole 40 may be in fluid communication with outlet 16 and hole 42 may be in fluid communication with inlet 18. In order to provide fluid communication between passageways 41, according to one aspect of the invention, plate 36 may include a plurality of relief grooves 44 which permit the passage of gas from one passageway 41 to the adjacent passageway 41. Arrows 46 in FIG. 6 illustrate the typical path of the flow of vacuum through grooves 44 and about ribs 36. According to one aspect, a recess 52 in end plates 22 and 24 may be provided. The surface of recess 52 may provide a sealing barrier to the passage of gas about grooves 44. A gasket or an adhesive may be provided in the recess 52 of end plates 22 and 24, for example, about the periphery of recess 52, to minimize leakage of treatment gas, for example, vacuum.

Support structure 34 may be fabricated by any conventional fabrication processes, for example, by welding, forging, casting, machining, and the like. According to one aspect of the invention, support structure 34 may also be fabricated by means of extrusion. For example, in one aspect of the invention, ribs 36 may be laterally or longitudinally mounted to plate 38 and ribs 36 and plate 38 may be fabricated by extrusion in a direction substantially parallel to the direction of elongation of ribs 36. Support structure 34 may be provided by a single integral structure. In other aspects of the invention, for example, as shown in FIG. 2, support structure 34 may be provided by two or more substructures 34', for example, two or more substantially identical substructures 34', to facilitate fabrication by, for example, extrusion.

Support structure 34 may be fabricated from any structural metal or non-metal. For example, support structure 34 may be fabricated from iron, steel, stainless steel, aluminum, titanium, nickel, magnesium, brass, bronze, or any other structural metal. Support structure 34 may also be fabricated from plastic, for example, a polyamide (PA), for instance, nylon; a polyethylene (PE); a polypropylene (PP); a polyester (PE); a polytetraflouroethylene (PTFE); an acrylonitrile butadiene styrene (ABS); a polycarbonate (PC); or a polyvinylchloride (PVC), among other plastics. Support structure 34 may be fabricated from an extrudable material, for example, aluminum alloy 6063 T5, or its equivalent.

Membrane 32 may be retained on support structure 34 by conventional means, for example, by means of mechanical fasteners or by means of adhesives. Membrane 32 may be retained in support structure 34 by means of elastomeric cords or rods 35, which may be referred to as "gaskets" in aspects of the invention. According to aspects of the present invention, gaskets 35 may be adapted to engage and retain membrane 32 in recesses in support structure 34 or in end plates 22 and 24. As shown in FIG. 3, end plates 22 and 24 may include elongated channels 49 that are adapted to receive a portion of membrane 32 and gaskets 35 whereby gaskets 35 are retained in channels 49 to retain membrane 32 against support structure 34. In addition to retaining membrane 32, gaskets 35 may provide a sealing means about the sides of support structure 34, for example, to isolate the vacuum provided in channels 41 from the gas passing through treatment zone 30.

According to one aspect of the invention, gaskets 35 may comprise any elastomeric material that can be adapted to be inserted into dehumidifier 10. Gaskets 35 may be natural rubber, neoprene, chloroprene, ethylene-propylene rubber (EDM/EPDM), urethane, polyurethane, styrene-butadiene rubber (SBR), isoprene rubber (IR), butadiene rubber (BR), room-temperature vulcanizing (RTV) silicone rubber, among other synthetic rubber or compounds. Gaskets 35 may be relatively "soft," for example, having a firmness of between about 8-9. For example, gaskets 35 may be silicone rubber foam cord, for instance, 5304 LCS Medium Density Low Compression Set Closed Cell Silicone Sponge provided by Groendyk Manufacturing Company, Inc. of Buchanan, Va., or its equivalent.

As shown in FIGS. 1 through 4, dehumidifier 10 also includes end plates 22 and 24. According to aspects of the invention, end plates 22 and 24 provide various functions, including providing structural support for the membrane support structures 34 and providing an enclosure for retaining the vacuum envelope provided in aspects of the invention. As shown most clearly in FIGS. 3 and 4, end plates 22 and 24 may be adapted to engage each other and provide the structural support and sealed vacuum envelope desired. End plates 22 and 24 may include complementary structures that interlock with each other. For example, end plates 22 and 24 may include projections 48 and channels 50 that are engageable to provide a substantially sealed structure. As shown in FIG. 2, projections 48 and channels 50 may extend along the entire length of end plates 22 and 24. The interface between projections 48 and channels 50 may include a sealing means, for example, a gasket or sealant, which minimizes or prevents leakage passed the interface. End plates 22 and 24 may also include a recess 52 adapted to receive support structures 34. Recess 52 may also be adapted to receive a sealing material, for example, an elastomeric gasket, to hinder or prevent the passage of vacuum from about support structure 34. As discussed above, end plates 22 and 24 may also include channels 49 adapted to receive membrane 32 and gaskets 35. End plates 22 and 24 may also include one or more holes 51 that may be used for assembling humidifier 10. For example, holes 51 may coincide with holes 67 in flange portions 64 and 66 of end caps 26 and 28 (discussed below) and accept mechanical fasteners 69, for example, bolts or screws, for mounting end caps 26 and 28 to end plates 22 and 24. In one aspect, where end plates 22 and 24 are fabricated by extrusion, holes 51 may be formed during extrusion or may be machined after extrusion.

According to aspects of the invention, endplates 22 and 24 may be made from one or more of the metals or non-metals listed above with respect to support structure 34 and fabricated by means of one or more of the fabrication processes listed above with respect to support structure 34. Endplates 22 and 24 may be fabricated by extrusion and made from an extrudable material, for example, aluminum alloy 6063 T1, or its equivalent. Endplates 22 and 24 may be fabricated from the same extrusion, cut to length, and oriented accordingly to engage projections 48 with recesses 50.

In one aspect, end plates 22 and 24 may include through holes 54, see FIG. 2, to which outlets 16 and inlets 18 may be mounted. Outlets 16 and inlets 18 may comprise any type of appropriate fitting. For example, outlet 16 and inlet 18 may each include a pipe nipple 56, a 90-degree elbow 58, and coupling 60, for example, a quick-disconnect coupling. Also, a single fitting having an NPT swivel elbow with an instant tube coupler may also be used.

As shown in FIGS. 1-3, dehumidifier 10 also includes two end caps 26 and 28. End caps 26 and 28 provide a structure to which to mount end plates 22 and 24, provide an interface for inlet 12 and outlet 14, complete the vacuum envelope, and also, according to one aspect, provide the transitional flow path for the gas flowing into and out of humidifier 10. End caps 26 and 28 may be substantially structurally identical, though in other aspects, end caps 26 and 28 may be different in structure.

Figure 7:
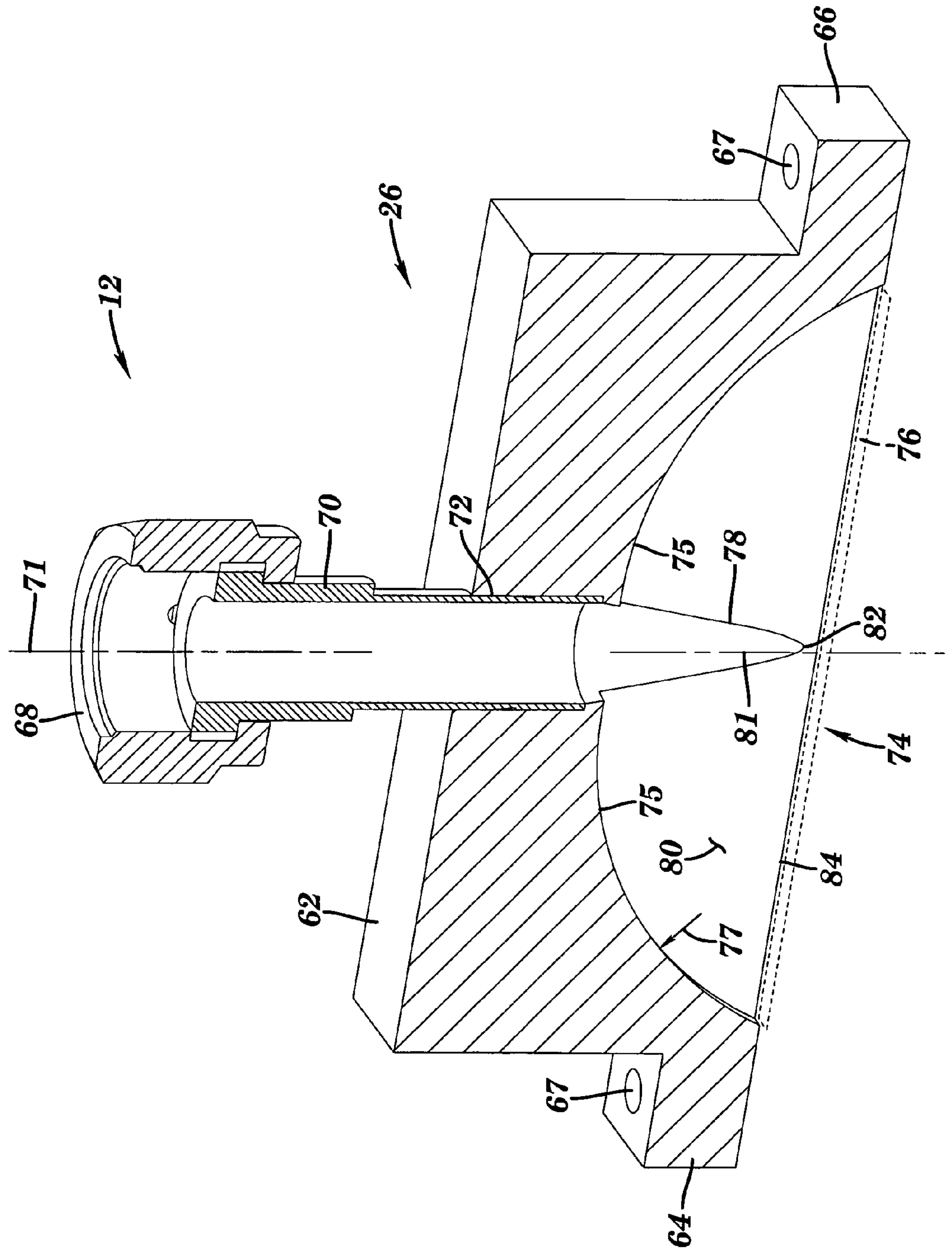
FIG. 7 is a perspective cross sectional view of one end cap shown in FIGS. 1-3 as viewed along section lines 7-7 in FIG. 3 according to one aspect of the invention.
Figure 8:
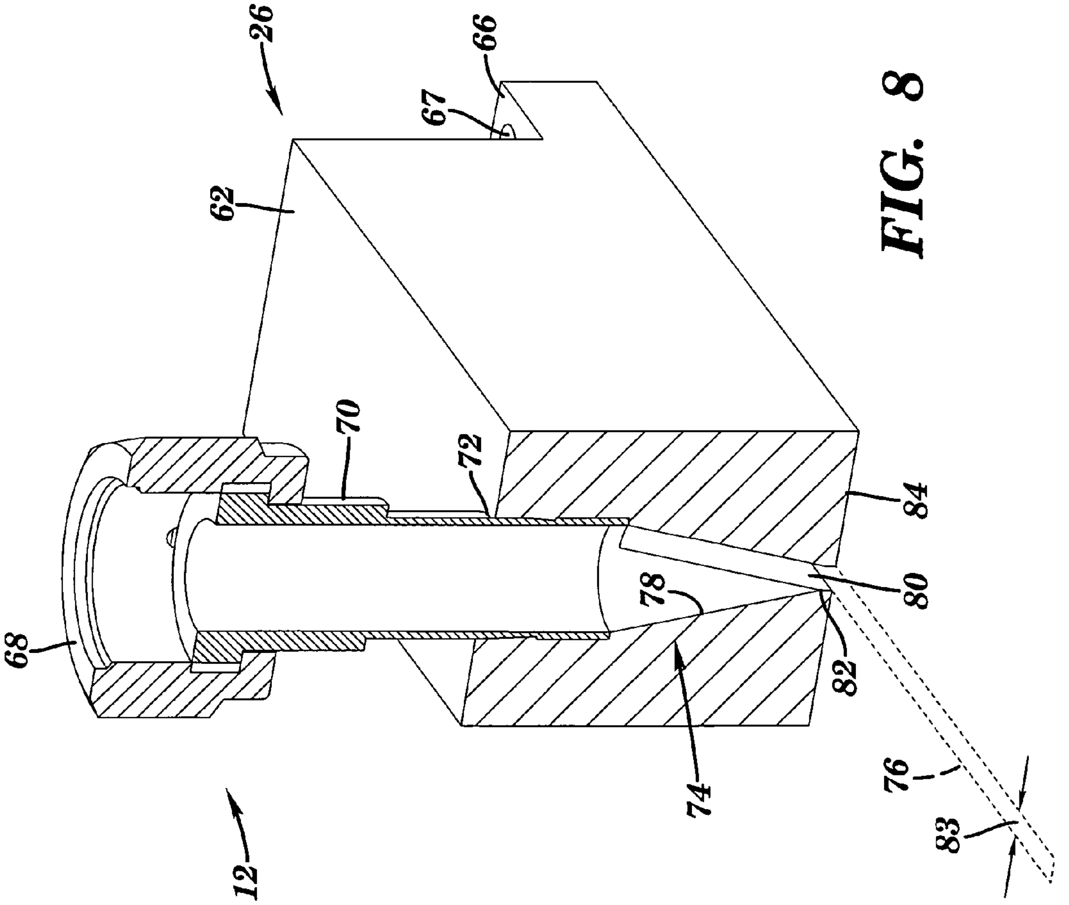
FIG. 8 is a perspective cross sectional view of the end cap shown in FIG. 7 as viewed along section lines 8-8 in FIG. 3.

The following discussion references end cap 26 in FIG. 2, but may also apply to end cap 28 in FIG. 2. As shown in FIG. 2, end cap 26 comprises a main body portion 62 and two flange portions 64 and 66. As shown in FIGS. 1-3, gas inlet 12 is mounted to main body portion 62, for example, by means of a press fit, by soldering, by brazing, by welding, by means of an adhesive (for instance, an epoxy) or by a threaded connection. FIG. 7 is a perspective cross sectional view of one end cap 26 as viewed along section lines 7-7 in FIG. 3 according to one aspect of the invention. FIG. 8 is a perspective cross sectional view of end cap 26 according to one aspect of the invention as viewed along section lines 8-8 in FIG. 3. As shown in FIGS. 7 and 8, gas inlet 12 comprises a coupling 68 mounted to a conduit 70 that is mounted in a hole 72 in main body portion 62. According to aspects of the present invention, beneath conduit 70, main body portion 62 includes a transitional flow path 74 that transitions the flow of gas from the circular cross section of conduit 70 to rectangular cross section 76, as shown in phantom in FIGS. 7 and 8. Cross section 76 may be orthogonal to axis 71 of conduit 72, as shown in FIGS. 7 and 8. Transitional flow path 74 provides an increase in the cross sectional area of the flow path of at least about 10%, typically, at least about 50%, and maybe even at least about 100%. Rectangular cross section 76 is substantially aligned with treatment zone 30 shown in the cross section of dehumidifier 10 shown in FIG. 4. According to one aspect of the present invention, transitional flow path 74 provides a transition in flow path geometry from the circular cross section of conduit 70 to the cross section 76, for example, a rectangular cross section, while minimizing or preventing particles from contacting surfaces to which the particles may collect or adhere. In another aspect, transitional flow path 74 may minimize or prevent the loss of pressure through the transitional flow path 74, and through humidifier 10. Though many diverse transitional flow paths 74 may be used to effect this desired performance, the cross sections of one typical flow path according to aspects of the invention are shown in FIGS. 7 and 8.

As shown in FIGS. 7 and 8, transitional flow path 74 comprises a tapered bore 78 of hole 72 where (recalling that FIGS. 7 and 8 illustrate cross sections of end cap 26) the diameter of hole 72 gradually diminishes. Transitional flow path 74 also includes a semicircular recess 80 in main body portion 62. Recess 80 may have an axis 81 that is substantially collinear with the axis 71 of conduit 70. In the aspect shown in FIG. 7, flow path 74 includes curvilinear surfaces 75, for example, a curvilinear surface having a radius 77, though any curvilinear surface, for example, an elliptical, a parabolic, or a hyperbolic curvilinear surface may be provided. In one aspect, the geometry of flow path 74 provides a gradual transition in the rectangular cross sectional area of flow path 74 over the length of end cap 26. According to one aspect of the invention, the gas entering conduit 70 expands into recess 80 while, as shown in FIG. 8, the diameter of tapered bore 78 diminishes to the diameter substantially equal to the width 83 of recess 80. The geometry of tapered bore 78 may create a gradual transition from the larger diameter of conduit 70 to the narrow rectangular cross section 76. As shown in FIGS. 7 and 8, the point 82 at which the diameter of tapered extension 78 converges to width 83 of recess 80 may be above the bottom 84 of main body portion 62. The geometry of the inlet end cap 26 and outlet end cap 28 may be substantially identical. Inlet end cap 26 functions to gradually expand the sample stream into the drying area of dehumidifier 10 and the outlet end cap 28 functions to converge the gas flow into the round conduit 70 at the outlet of dehumidifier 10. At least one of end caps 26 and 28 may be fitted with a relative humidity sensor (not shown), for example, to provide a measure of the performance of dehumidifier 10.

Figure 9:
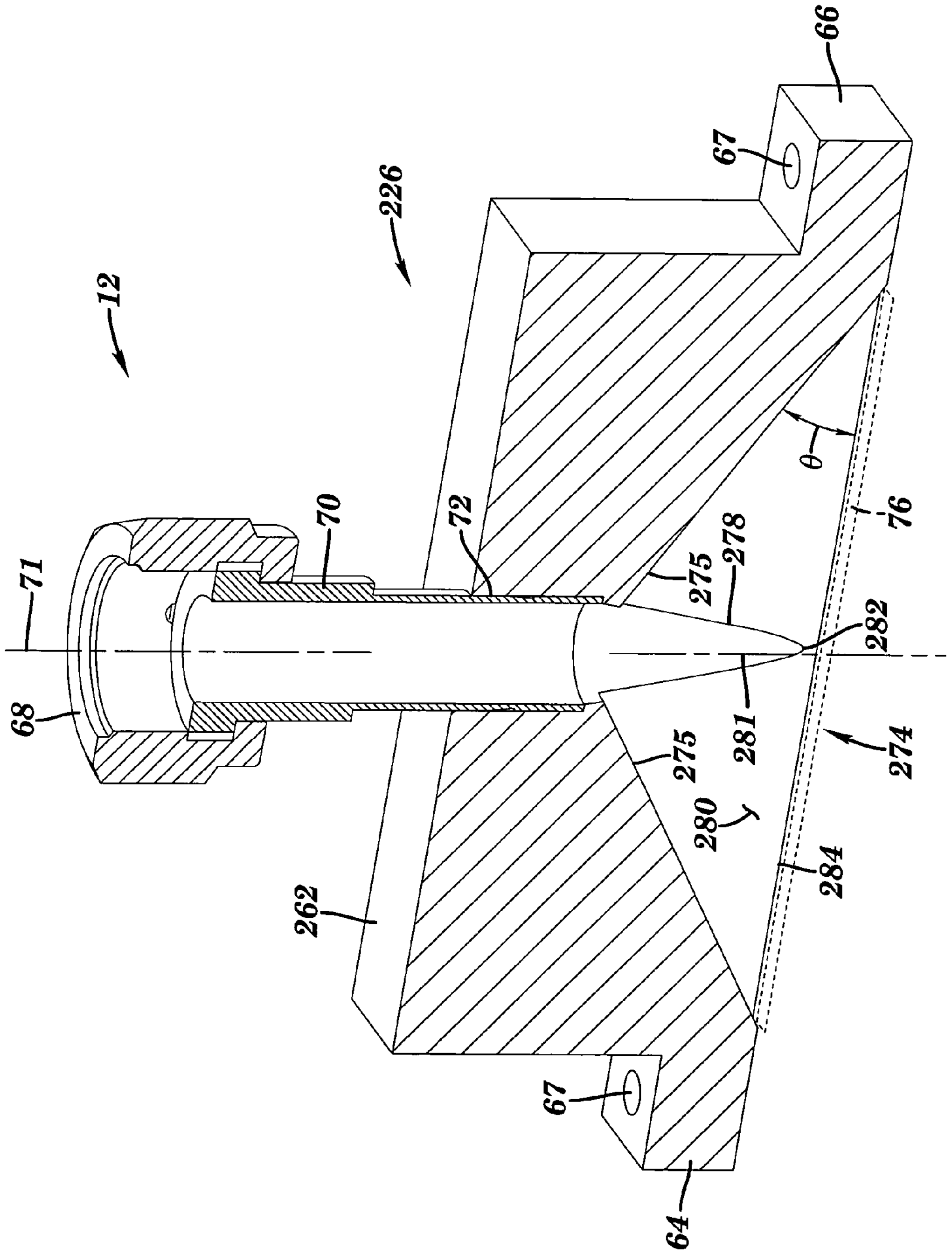
FIG. 9 is a perspective cross sectional view, similar to FIG. 7, of another end cap as viewed along section lines 7-7 in FIG. 3 according to another aspect of the invention.
Figure 10:
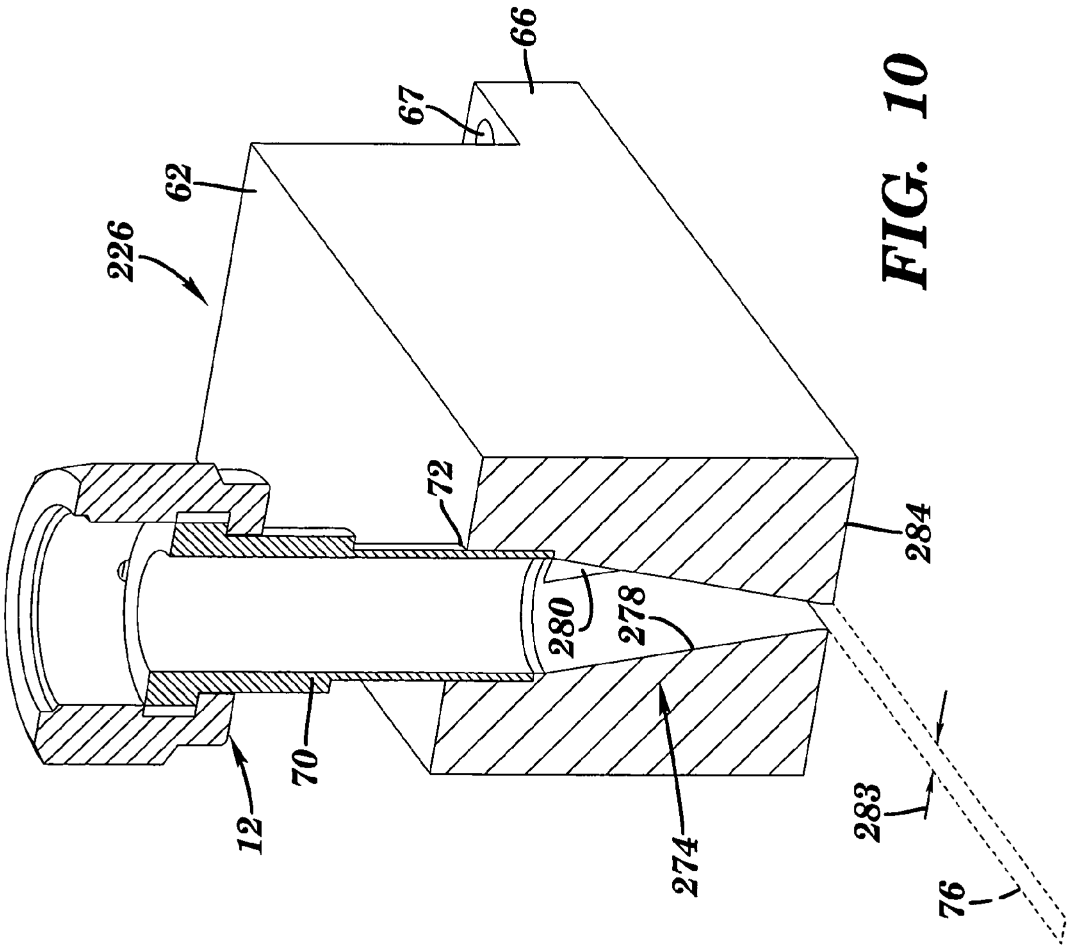
FIG. 10 is a perspective cross sectional view, similar to FIG. 8, of the end cap shown in FIG. 9 as viewed along section lines 8-8 in FIG. 3.

FIG. 9 is a perspective cross sectional view, similar to FIG. 7, of another one end cap 226 as also viewed along section lines 7-7 in FIG. 3 according to another aspect of the invention. FIG. 10 is a perspective cross sectional view, similar to FIG. 8, of end cap 226 as also viewed along section lines 8-8 in FIG. 3. Again, though many diverse transitional flow path geometries may be used to provide a flow path transition from the inlet to the treatment zone according to aspects of the invention, FIGS. 9 and 10 illustrate one transitional flow path. Many of the features of end cap 226 are substantially similar or even identical to the features of end cap 26 shown in FIGS. 7 and 8. These similar or identical features are identified by the same reference numbers in FIGS. 9 and 10.

As shown in FIGS. 9 and 10, end cap 226 includes substantially all the features of end cap 26, including gas inlet 12, conduit 70 mounted in a hole 72 in main body portion 262. According to aspects of the present invention, beneath conduit 70, main body portion 262 includes a transitional flow path 274 that, similar to transition 74 in FIGS. 7 and 8, transitions the flow of gas from the circular cross section of conduit 70 to the rectangular cross section 76, shown in phantom in FIGS. 9 and 10. According to aspects of the present invention, transitional flow path 274 provides a transition in flow path geometry from the circular cross section of conduit 70 to the rectangular cross section 76 while minimizing or preventing particles from contacting surfaces to which the particles may collect or adhere. Transitional flow path 274 may minimize or prevent the loss of pressure through the transitional flow path 274, and through humidifier 10. Again, though many diverse transitional flow paths 274 may be used to effect this desired performance, the cross sections of one typical flow path according to aspects of the invention are shown in FIGS. 9 and 10.

As shown in FIGS. 9 and 10, transitional flow path 274 comprises a tapered bore 278 of hole 72 where (recalling that FIGS. 9 and 10 illustrate cross sections of end cap 226) the diameter of hole 72 gradually diminishes. Transitional flow path 274 also includes a triangular recess 280 in main body portion 62 having a vertical axis 281 that is substantially collinear with the axis 71 of conduit 70. In the aspect shown in FIG. 9, flow path 274 includes linear surfaces 275 that make an angle, θ, of between about 30 degrees and 60, for example, about 45 degrees, with the base 284 of end cap 226. The geometry of flow path 274 may provide a gradual transition in the rectangular cross sectional area of flow path 274 over the length of end cap 226. According to one aspect of the invention, the gas entering conduit 70 expands into recess 280 while, as shown in FIG. 10, the diameter of tapered bore 278 diminishes to the diameter substantially equal to the width 283 of recess 280. The geometry of tapered bore 278 may create a gradual transition from the larger diameter of conduit 70 to the narrow rectangular cross section 76. As shown in FIGS. 9 and 10, the point 282 at which the diameter of tapered extension 278 converges to width 283 of recess 280 may be above the bottom 284 of main body portion 262.

According to aspects of the invention, end caps 26, 28, 226, and 228 may be made from one or more of the metals or non-metals listed above with respect to support structure 34 and fabricated by means of one or more of the fabrication processes listed above with respect to support structure 34. According to one aspect of the invention semicircular recess 80 may be fashioned in main body portion 62 by means of a circular saw cut. End caps 26 and 28 may be machined from solid material for example, machined from 6061 T6 aluminum alloy, or its equivalent.

In one aspect, end caps 26, 28, 226, and 228 are designed to provide a low particulate loss transition from round sample conduits to a rectangular dehumidifier cross section, then back to round conduits. At least two distinct machining operations may be used to create the end cap geometry shown in FIGS. 7 and 8. The first operation may be a saw cut into the edge of a block of material intended to be fashioned into end cap 26. This cut creates the rectangular cross section of recess 80 having radius 77. A saw cut enables a gradual transition in rectangular cross section cross sectional area over the length of end cap 26 that characterizes recess 80. The second operation may be the creation of the tapered bore 78 through the center of end cap 26, substantially parallel to the sample flow path of conduit 70. The geometry of bore 78 creates a gradual radial transition from the larger diameter sample tube 70 to the narrow rectangular cross section 76. End cap 26 may be fabricated from two or more piece parts and, for example, recess 80 may be machined into one or more piece parts of end cap 26 and then mated, for example, by mechanical fasteners or welding, to provide the desired flow path 74. The geometry of the inlet end cap 26 and outlet end cap 28 may be substantially identical. End cap 26 acts to gradually expand the sample stream into the dehumidifying or treatment zone 30 of dehumidifier 10 and end cap 28 acts to converge the gas stream into the round conduit 70 in outlet 14.

As shown in FIGS. 3 and 7, flange portions 64 and 66 of end caps 26, 28, 226, and 228 may include means for assembling end caps 26 and 28 to humidifier 10. For example, flange portions 64 and 66 may include one or more holes 67 for accepting fasteners, for instance, bolts or screws, which engage holes 51 in end plates 22 and 24, though other conventional attachment means may be used.

Referring back to FIG. 2, according to one aspect of the invention, humidifier 10 may also include some form of gas sealing means between end caps 26 and 28 and the rest of the components of humidifier 10. Gaskets 84, for example, elastomeric gaskets, may be positioned on the inboard side of end caps 26 and 28 to minimize or prevent the leakage of gases between the mating surfaces of end caps 26 and 28 and membrane support structure 34, between the mating surfaces of end caps 26 and 28 and membrane end plates 22 and 24, and between the mating surfaces of end caps 26 and 28 and membranes 32. Membrane 32 may be longer in length than support structure 34 whereby a portion of membrane 32 may be folded over the end of support structure 34 to effectively seal this interface with gaskets 84 when assembled. Gaskets 84 may be typically perforated to avoid obstructing holes 67 and recess 80 in end caps 26 and 28. According to one aspect of the invention, elastomeric gaskets 84 may be silicone rubber sheets having a 40A durometer hardness provided by Reiss Manufacturing, Inc. of Blackstone, Va., or its equivalent.

In the aspects of the invention shown in FIG. 1-10, dehumidifier 10 typically is shown and described as having a single gas treatment zone 30, as shown in FIG. 4. However, according to one aspect of the invention, dehumidifier 10 may have a plurality of treatment zones 30, each treatment zone bounded by at least one water vapor permeable membrane 32, for example, two membranes. According to one aspect of the invention, the plurality of treatment zones 30 may be positioned parallel to each other. Each treatment zone 30 may comprise two membranes 32 mounted on respective individual support structures 34 mounted adjacent to each other. In another aspect of the invention, two support adjacent structures 34 may be integrated into a single support structure comprising a plate 38 and ribs 36 mounted to either side of the plate in one of more rib configurations discussed above.

In one aspect of the invention having a plurality of treatment zones 30, end caps 26 and 28 may comprise a plurality of end caps each of the plurality of end caps having inlets 12 and outlets 14. End caps 26 and 28 may comprise individual inlets 12 and outlets 14, wherein end caps 26 and 28 may comprise manifolds or gas distribution paths that distribute the gas introduced to one or more inlets 12 to the plurality of treatment zones 30 and collect the gas from the plurality of treatment zones 30 and direct it to the one or more outlets 14. Appropriate sealing means, for example, sheet or rope gaskets, may be provided to seal the respective gas passages as appropriate. The plurality of purge sides of the flow passages may be provided with a source of vacuum, for example, via a plurality of vacuum sources or via vacuum distribution passages or conduits internal or external to dehumidifier 10. Other scaled up adaptations of aspects of the invention will be apparent to those of skill in the art including the deployment of multiple dehumidifiers 10 in parallel or series.

According to aspects of the present invention, the diffusion of water vapor across membrane 32, for example, a Nafion membrane, may typically be driven by a water vapor concentration gradient over membrane 32. In the following discussion, the side of membrane 32 against which sample gas stream 15 (see FIG. 1) flows will be referred to as the "sample side" 21 (see FIG. 3) of membrane 32 and the side of membrane 32 against which treatment gas stream 25 (see FIG. 1) flows will be referred to as the "purge side" 23 of membrane 32. In one aspect of the invention, the desired water vapor concentration gradient may be created by expanding a gas under vacuum and passing the expanded gas to purge side 23 of membrane 32. For example, a lower water vapor concentration may be provided by expanding a flow of gas on the low-pressure side, or downstream side, of a flow control device, for example, a valve, though other types of pressure reducing devices may be used. Expanding a gas stream may provide sufficiently lower water vapor concentration in the resulting gas stream to provide a sufficient concentration gradient desired across membrane 32 according to aspects of the invention. After expansion, the lower pressure gas stream may be introduced to purge side 23 of membrane 32 to provide the desired water vapor concentration gradient. The gas stream 17 (see FIG. 1) exiting sample side 21 of dehumidifier 10 may be expanded, for example, by passing gas stream 17 through a flow control device, and then introduced as the source of lower water vapor concentration medium on purge side 23 of membrane 32. The expanded gas stream will accept water vapor through membrane 32 and exit dehumidifier 10 with the water vapor from the gas on sample side 21 of membrane 32. As discussed below, the flow of gas through dehumidifier 10 may be provided by a source of vacuum, for example, a vacuum pump.

The direction of sample gas flow 15 may be provided whereby the treatment or purge gas flow 25 may be substantially opposite in direction to the direction of sample gas flow 15. In aspects of the invention, the inventors have found that providing this opposite, or counter-current, flow of gases in which the driest purge gas flow 25 is introduced at the location in dehumidifier 10 where the driest sample gas flow 15 is present provides improved water vapor removal from gas stream 15. In another aspect of the invention, the respective gas flows may be provided in substantially the same direction through dehumidifier 10, that is, in a co-current or non-counter-current flow arrangement.

In one aspect of the invention, the source of vacuum, for example, a vacuum pump, may be the only energy introduced to dehumidifier 10 or to a system incorporating dehumidifier 10, as will be described more completely below. According to one aspect of the invention, the greater the vacuum provided to purge side 23 of membrane 32, the higher the dehumidifying efficiency of dehumidifier 10, for a given flow rate.

Dehumidifier 10, 110 may be operated with substantially the same mass flow rate through sample side 21 (see FIG. 3) and through purge side 23. The mass flow rates of the sample gas stream 15 (see FIG. 1) and purge gas stream 25 may be different, for example, sample stream 15 may have a greater mass flow rate than purge gas stream 25 or sample gas stream 15 may have a lower mass flow rate than purge gas stream 25. In one aspect, for example, when purge side gas flow 25 is first expanded, for example, greatly expanded, for instance, after the gas exits the sample side 21 of dehumidifier 10, the volumetric flow of sample gas stream 15 may be less, for example, far less, than the volumetric flow rate of the purge gas stream 25 in dehumidifier 10. In one aspect, the sample gas stream 21 is expanded by vacuum after it exits dehumidifier 10, 110 and before it becomes the purge gas stream 25. As a result, the purge gas stream 25 may occupy a much larger volume than the sample gas stream 15, that is, the volumetric flow of the sample gas stream 15 may be much less than volumetric flow of the purge gas stream 25.

According to aspects of the invention, dehumidifier 10, 110 provides improved dehumidification while minimizing the impact upon particulate transfer through dehumidifier 10, 110. For example, passing a sample gas stream having a content of particulate matter, for example, PM-10 particulate matter or less, through dehumidifier 10 may produce a dehumidified gas stream having at least about 60% of the particulate matter introduced to dehumidifier 10. However, the efficiency of the transfer of particulate matter through dehumidifier 10 may vary as a function of particulate matter size and or particulate matter velocity, among other things. In one aspect, for a given particulate matter size and/or velocity at least about 80% of the particular matter is retained, or at least 90% of the particulate matter is retained, or 95% of the particulate matter is retained, or even 99% of the particulate matter is retained. In one aspect of the invention, no particulate matter is lost during the dehumidification process and the dehumidified gas stream may contain substantially 100% of the particulate matter introduced to dehumidifier 10, 110.

According to aspects of the invention, the geometries of the flow paths 74 and 274 of the sample side gas flow 15 of humidifier 10 are provided to achieve this high particle retention. Sample side gas flow paths 74 and 274 of dehumidifier 10 may promote high quality gas flow with gradually transitioning flow path cross sections. Computer aided analysis, specifically, computational fluid dynamic analysis, suggests that aspects of the present invention provide little or no gas flow separation on sample gas flow, for example, gas flow separation that may cause particles, for example, PM-10 and smaller particles, to exit the flow stream and impact or be deposited on the internal surfaces of dehumidifier 10.

The flow geometries and cross sections in purge side 23 may be of little or no importance with regards to particle retention in dehumidifier 10. For example, the desired particulate analysis on the gas stream sample 15 may have already been performed, that is, prior to the gas stream entering purge side 23 of dehumidifier 10. However, the geometry of the flow path through purge side 23 may affect the operation of dehumidifier 10, for example, high velocity gas flows and/or turbulent gas flow though the flow path on purge side 23 may enhance the passage of water vapor through membrane 32. High velocity gas flows and/or turbulent gas flow may also promote minimal boundary layer development on purge side 23 of membrane 32. According to one aspect of the invention, the formation of a boundary layer on the purge side of membrane 32 may be minimized or prevented. It is understood that minimizing or preventing boundary layer formation on the purge side of the membrane enhances water vapor transfer through the membrane. In one aspect, an indirect, or circuitous, or serpentine gas flow path may be provided, for example, as shown in FIGS. 5 and 6, to, for example, accelerate the flow of gas through the purge side 23 and minimize the formation of a boundary layer in the dehumidifier 10. The minimization or prevention of the formation of a boundary layer may be provided by creating turbulent flow of gas on the purge side 23 of membrane 32. In one aspect, the velocity of flow through the purge side 23 to provide the desired turbulent flow may be at least about 15 meters per second [m/s], or greater, for example, 30 m/s, or 45 m/s, or greater.

In another aspect of the invention, the effective surface area of membrane 32 may affect the efficiency of the dehumidification. The effective surface area of membrane 32 is the area of the sample side 21 of the membrane that functions to pass water vapor to the purge side 23 of membrane 32. Within the size constraints established to produce a dehumidifier, or "dryer," 10 of reasonable dimensions, the effective surface area of membrane 32, for example, of a Nafion membrane, may be directly proportional to the concentration of water vapor in the gas discharged from outlet 14. Analysis and testing of aspects of the invention suggest that there may an effective membrane area beyond which dehumidification efficiency does not increase with increasing effective surface area—that is, a point of diminishing returns on increased effective membrane area.

In one aspect of the invention, the thickness of membrane 32 may also influence the effectiveness of dehumidifier 10. Specifically, an interrelationship may exist between water vapor removal efficiency and component durability. For example, membranes 32 having a thickness of about 0.002" appear to satisfy this balance between water vapor removal efficiency and component durability. The optimum membrane thickness may vary depending upon the size and operating conditions of dehumidifier 10.

In another aspect of the invention, separation distance 33 between membranes 32 (see FIG. 4) may influence the effectiveness of dehumidifier 10. Specifically, an interrelationship may exist between the velocity of the sample flow through dehumidifier 10 and the efficiency of the water removal in dehumidifier 10. Both gas velocity and residence time may be functions of separation distance 33, among other things. For example, contrary to intuition, in some aspects of the invention, as the velocity of the sample gas through dehumidifier 10 increases, for example, by decreasing the separation distance 33 between membranes 32, the ability of dehumidifier 10 to remove water vapor may increase. This direct relationship between velocity and water vapor removal efficiency may be limited. For example, there may exist a condition above a certain flow velocity where water removal efficiency does not increase, but may plateau or decrease. The transition velocity may vary with the size (for example, width), separation distance 33, and operating conditions of dehumidifier 10. For example, dehumidifier 10 may be designed to operate at an optimum water removal efficiency over a range of design flow rates, for example, for a design flow rate of between about 0.5 liters/minute and about 4.0 liters/minute, but is typically designed for flow rates of between about 1.0 liter/minute and about 3.0 liters/minute.

Figure 11:
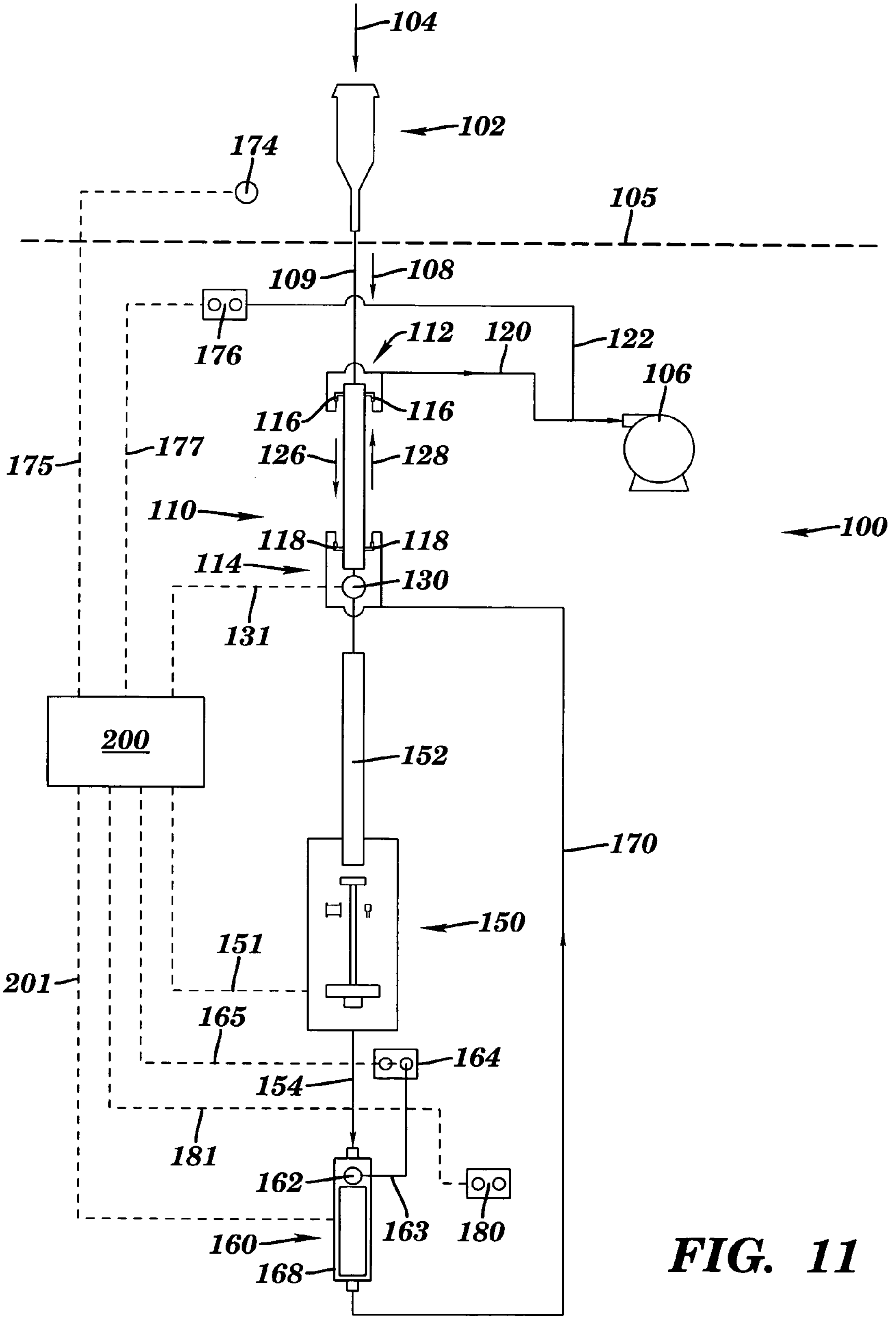
FIG. 11 is schematic illustration of a particulate matter sampling system for a gas stream according to another aspect of the invention.

FIG. 11 is schematic illustration of a particulate matter sampling system 100 for sampling a gas stream according to another aspect of the invention. System 100 may be adapted to sample air streams for the presence of many types of particles, for example, organic particles, such as pollen and other allergens, and inorganic particles, such as, sand, dust, smoke, automobile exhaust, and the like. System 100 includes a dehumidifying device 110, for example, dehumidifier 10 shown in FIGS. 1-10, or its equivalent, though other types of dehumidifying devices may be used. System 100 may include a mass measuring device 150, a mass flow controller 160, and an electronic controller 200.

System 100 typically includes a gas inlet device 102, for example, size-selective gas inlet device. Inlet device 102 may be a size-selective gas inlet device adapted to select particles ranging from PM-10, PM-2.5, PM-1 to TSP (total suspended particulate matter). Size selective inlet 102 may be provided by Thermo Electron Corporation, though other similar or related devices may be used. Gas inlet device 102 may be adapted to accept a gas stream sample, as indicated by arrow 104. Gas sample 104 may be an outside air sample, an inside air sample, or a sample taken from a controlled environment, for example, taken from a chamber in a test facility or laboratory, among other sources. Gas inlet device 102 may be positioned outside of a building, as indicated by phantom line 105, for example, on the roof of a building, such as a commercial building or residential home. System 100 may be mounted on a portable platform, such as a trailer. Gas inlet device 102 may be designed and operated at a gas flow rate of about 16.7 liters/minute (that is, about 1 $m^3$/h).

System 100 may include a temperature and/or relative humidity sensor 174 adapted to provide an indication of the temperature and humidity of the ambient air, and thus of gas sample stream 104. Sensor 174 may be a model SHT11 temperature and humidity sensor provided by Sensirion AG of Staefa, Switzerland, though other similar or related devices may be used. The temperature and/or humidity detected by sensor 174 may be transmitted to electronic controller 200 via electrical connection 175, for example, by means of a 0-5 Volt DC (VDC) or 4-20 milliamp (mA) signal.

Gas stream 104 may be directed into system 100 under pressure, for example, provided by a blower or fan (not shown) or by a vacuum. In the aspect of the invention shown in FIG. 11, gas stream 104 is drawn into system 100 by means of a source of vacuum 106, for example, a vacuum pump or an ejector. The source of vacuum 106 may be a vacuum pump and, though other sources of vacuum or pressure may be used to introduce gas stream 104 to system 100, to facilitate disclosure of the invention, the following discussion will refer to the motive force as a source of vacuum and the specific source of vacuum 106 as a vacuum pump.

Vacuum pump 106 may be any commercially available vacuum pump capable of providing at least 10 inches of Hg vacuum, for example, at least 20 inches of Hg vacuum. Vacuum pump 106 may be a Model 2688CE44 vacuum pump provided by Thomas Industries of Sheboygan, Wis., though other similar or related devices may be used. The path or flow of the vacuum provided by vacuum pump 106 will be discussed below.

As indicated by arrow 108 in FIG. 11, as will be discussed below, vacuum pump 106 draws gas stream 104 through inlet device 102 and through conduit 109 and into dehumidifier 110. According to this aspect of the invention, dehumidifier 110 may comprise a membrane type dehumidifier wherein the membrane (not shown) comprises a material that is permeable to water vapor, for example, DuPont's Nafion® PFSA, or its equivalent. According to one aspect of the invention, dehumidifier 110 includes a flow path for gas stream 104 bounded by one side of the membrane and a flow path exposed to vacuum bounded by the other side of the membrane. According to one aspect of the invention, dehumidifier 110 may be any type of dehumidifier that may be adapted to function according to the present invention. Dehumidifier 110 may be a parallel plate type dehumidifier. In another aspect of the invention, dehumidifier 110 may by a tube-type or a bundled-tube type dehumidifier. Similar to dehumidifier 10 shown and discussed with respect to FIGS. 1-10, dehumidifier 110 includes an inlet 112, and outlet 114, at least one outlet 116, and at least one inlet 118. According to aspects of the present invention, outlet 116 may be operatively connected to vacuum pump 106 by means of conduit 120. The operation of vacuum pump 106 may be monitored by means of pressure sensor 176, for example, any device adapted to detect gage, absolute, or differential pressure. As shown in FIG. 11, one leg of the pressure sensor 176 may be operatively connected to the low pressure inlet of vacuum pump 106 via conduit 122 and the other leg of sensor 176 may be adapted to sense ambient pressure. Sensor 176 may be a model MPX4115AP pressure sensor provided by Freescale Semiconductor, Inc. of Austin, Tex., though other similar or related devices may be used. The pressure detected by sensor 176 may be transmitted to electronic controller 200 via electrical connection 177, for example, by means of a 0-5 Volt DC (VDC) or 4-20 milliamp (mA) signal.

Sensor 176 may provide an indication of the performance and/or operation of vacuum pump 106. For example, when the pressure indicated by sensor 176 drops below a predetermined value, for example, 20 inches of mercury (Hg) absolute, the operator may be advised by electronic controller 200, for example, to take appropriate action.

The flow of gas sample 104 through dehumidifier 110 is indicated by arrow 126, the flow of vacuum through dehumidifier 110 is indicated by arrow 128. In one aspect of the invention, to provide the desired water vapor concentration gradient, the flow of vacuum gas stream 128 typically may have a water vapor concentration at least about 5% lower than the water vapor concentration of the gas sample stream 126. The water vapor concentration of vacuum gas stream 128 may be at least about 10% lower, or even at least about 25% lower, or more, than the water vapor concentration of sample gas stream 126.

Though in one aspect of the invention, the flow of vacuum 128 may be opposite or counter-current to the flow of treated gas 126, in another aspect of the invention, these flows may be in the same or co-current direction. According to aspects of the present invention, as the gas stream 104 passes through dehumidifier 110, the water vapor concentration gradient across the membrane causes the water vapor to pass through the membrane from the water vapor rich gas stream 126 to the water vapor lean gas stream 128 in dehumidifier 110 whereby the treated gas stream exited outlet 114 of dehumidifier 110 contains less water vapor than the gas stream introduced into inlet 112. Similarly, according to aspects of the invention, the vacuum exiting dehumidifier 110 through outlet 116 typically may contain more water vapor than the vacuum introduced to inlet 118. Inlets 118 may be operatively connected to the outlet of a mass flow controller 160, for example, via conduit 170.

System 100 may include a relative humidity sensor 130 adapted to sense the relative humidity in system 100. Relative humidity sensor 130 may be positioned downstream of dehumidifier 110 and be adapted to sense the relative humidity of the gas stream exiting dehumidifier 110, for example, to estimate the performance of dehumidifier 110. Sensor 130 may be a SHT11 relative humidity sensor provided by Sensirion AG, though other similar or related devices may be used. The relative humidity detected by sensor 130 may be transmitted to electronic controller 200 via electrical connection 131, for example, by means of a 0-5 Volt DC (VDC) or 4-20 milliamp (mA) signal. System 100 may be operate to ensure a relative humidity of the gas stream exiting dehumidifier 110 of at least a target value, for example, at least a target relative humidity percentage (for example, at a given temperature) or at least a target dew point. For example, system 100 may be operative to provide at least a dew point about 2 degrees C at the outlet of dehumidifier 110, as indicated by sensor 130.

System 100 typically includes a mass measuring device 150 adapted to collect and/or detect the amount of particulate matter contained in a gas sample, indicated by arrow 104, after passing through dehumidifier 110. Mass measuring device 150 may be any mass measuring device adapted to collect, detect, or measure particulate matter in gas stream 104. Mass measuring device 150 may include a sample inlet tube 152. Mass measuring device 150 may be a real-time ambient particulate mass concentration measuring device, for example, a TEOM® Series 1400a Ambient Particulate Monitor provided by Thermo Electron Corporation. In another aspect of the invention, mass measuring device 150 may be a beta attenuation device adapted to collect particles or a filtering device adapted to collect particles which may be analyzed on-line or after removal of the filtering device. Other mass measuring devices may also be used. Mass measuring device 150 may be adapted to provide an electrical signal representative of the mass detected, for example, an indication of the frequency of vibration of the mass collecting element of mass collecting device 150, though mass indicative parameters may be provided. The signal corresponding to the mass detected by device 150 may be transmitted to electronic controller 200 via electrical connection 151, for example, by means of a 0-5 Volt DC (VDC) or 4-20 milliamp (mA) signal.

System 100 may also include a mass flow controller 160 that receives a flow of gas from mass measuring device 150 via conduit 154. Mass flow controller 160 may be any device adapted to regulate the flow of gas. Mass flow controller 160 may comprise a valve, for example, a solenoid, gate, ball, or any other type of valve. Mass flow controller 160 may be a mass flow controller provided by Thermo Electron Corporation, though other similar or related devices may be used. The operation of mass flow controller 160 may be regulated by electronic controller 200, for example, via electrical connection 201, for example, by means of a 0-5 Volt DC (VDC) or 4-20 milliamp (mA) signal. The operation of mass flow controller 160 may be regulated by electronic controller 200 as a function of temperature and/or humidity of the gas stream being treated, for example, as indicated by sensors 174, 130, and 180, among other system operating parameters.

System 100 may include a mass flow sensor 168 adapted to detect the flow of mass through system 100. Mass flow sensor 168 may be a Model AWM5101 mass flow sensor provided by Honeywell International Inc of Morristown, N.J., though other similar or related devices may be used. The output signal from mass flow sensor 168 may be transmitted to electronic controller 200, for example, via electrical connection 201, for example, by means of a 0-5 Volt DC (VDC) or 4-20 milliamp (mA) signal. The mass flow of gas through sensor 168 may be used to regulate the operation of mass flow controller 160. For example, the flow of mass through sensor 168 may regulate the operation of a valve in mass flow controller 160. Mass flow controller 160 and mass flow sensor 168 may be provided in a single integrated assembly or housing. In another aspect of the invention, mass flow controller 160 and mass flow sensor 168 may be provided in two or more separate housings.

The operation of mass measuring device 150 may be monitored by means of pressure sensor 164, for example, a any device adapted to detect gage, absolute or differential pressure. As shown in FIG. 11, one leg of the pressure sensor 164 may be operatively connected to the mass flow controller 160 via conduit 163 and the other leg of sensor 164 may be adapted to sense ambient pressure. Sensor 164 may be a model MPX4115AP pressure sensor provided by Freescale Semiconductor, Inc., though other similar or related devices may be used. The pressure detected by sensor 164 may be transmitted to electronic controller 200 via electrical connection 165, for example, by means of a 0-5 Volt DC (VDC) or 4-20 milliamp (mA) signal.

Sensor 164 may provide an indication of the performance and/or operation of mass measuring device 150. For example, when the pressure indicated by sensor 164 reaches a predetermined value, for example, about 7 inches of mercury (Hg) absolute, the operator may be advised by electronic controller 200, for example, to take appropriate action. For example, the pressure detected by sensor 164 may provide an indication of the state of the mass collecting unit of mass measuring device 150, for instance a pressure greater than a predetermined value may indicate that a collecting filter in device 150 may be fouled or otherwise malfunctioned.

System 100 may include one or more sensors for detecting ambient temperatures, ambient pressures, component temperatures, component pressures, gas flow rates, mass flow rates, and the like. For example, system 100 may include at least one ambient pressure sensor 180, for example, gage or absolute pressure. Sensor 180 may be a model MPX4115AP pressure sensor provided by Freescale Semiconductor, though other similar or related devices may be used. The pressure detected by sensor 180 may be transmitted to electronic controller 200 via electrical connection 181, for example, by means of a 0-5 Volt DC (VDC) or 4-20 milliamp (mA) signal.

The temperature sensed by sensor 174 and/or the ambient pressure sensed by sensor 180 may be used to regulate the operation of system 110, for example, regulate the operation of one or more of the components of system 100. For example, the temperature sensed by sensor 174 and/or the pressure sensed by sensor 180 may be used to regulate the operation of mass flow controller 160.

Monitoring and/or control of system 100 or its components may be performed by one or more electronic controllers 200. Electronic controller 200 may comprise a personal computer, a programmable logic controller, or a similar processing device adapted to receive data, record and/or manipulate data, and output information to a human operator or to other devices. For example, computer processor 200 may receive a temperature and a humidity signal from sensor 174 via electrical connection 175 or an atmospheric pressure signal from pressure detector 180 via electrical connection 181. Then, based upon a predetermined algorithm, computer processor 200 may output a control signal 201 to mass flow controller 160 to regulate the operation of mass flow controller 160, for example, to regulate the flow of gas through mass flow controller 160 —and thus through mass measuring device 150— by, for instance, opening or closing an orifice in mass flow controller 160. Other control means may also be provided to optimize the operation of system 100.

A differential pressure may exist across the membrane, for example, membrane 32, in dehumidifier 10 or 110. This differential pressure may be the motivating force for transferring water vapor across the membrane or this differential pressure may be one component of the motive force transferring water vapor across the membrane. For example, the differential pressure may augment or assist the water vapor concentration gradient across the membrane in effecting water vapor transfer. In one aspect of the invention, the relative difference in the gas vapor pressure may be the motivating force for transferring water vapor across the membrane. For example, the untreated gas stream may have a first vapor pressure and the treatment gas stream may have a second vapor pressure, lower than the first vapor pressure. In another aspect, the relative difference in absolute humidity, that is, the mass of water per volume of gas, may be the motivating force for transferring water vapor across the membrane. For example, the untreated gas stream may have a first absolute humidity and the treatment gas stream may have a second absolute humidity, lower than the first absolute humidity.

The particulate laden gas stream 126 flowing through the sample side of dehumidifier 10 or 110 may be exposed to a pressure less than atmospheric, or ambient, pressure, for example, slightly less than ambient pressure. This pressure drop from ambient pressure (for example, ambient pressure detected by pressure sensor 180) may be due to the flow restriction, though typically minimal, provided by the inlet device 102. In contrast, in one aspect, the pressure on the purge side 128 of the membrane of dehumidifier 10 or 110 may be created by the source of vacuum, for example, vacuum pump 106. The vacuum pressure provided on the purge side 128 of the membrane may be as large as can be provided by the vacuum pump 106 at the flow that the vacuum pump 106 is being operated. The drying efficiency of dehumidifier 10 or 110 may increase as the vacuum provided by vacuum pump 106 increases. The vacuum pressure provided on the purge side 128 of dehumidifier 10 or 110 may be at least 20 inches of mercury (Hg) or greater, for example, 30 inches of Hg, or more, though water vapor may be transferred at lower levels of vacuum. According to aspects of the invention, the value of the sub-atmospheric pressure drawn by the source of vacuum (and any other pressure value provided herein) may be relative to atmospheric pressure in inches of Hg, for example, relative to about 29.921 inches of Hg at 0 degrees C. That is, a pressure of about 20 inches of Hg corresponds to about 20 inches of Hg below atmospheric pressure, or about 9.921 inches of Hg absolute pressure.

The vacuum pressure in the purge side 128 of dehumidifier 10 or 110 may also act as the force to keep the membrane, for example, membrane 32, flat against the membrane support structure (for example, flat against the ribs 36 of support structure 34 shown in FIG. 2). The minimum pressure differential across the membrane in dehumidifier 10 or 110 may be about 3 to about 5 inches of Hg.

Though in one aspect of the invention, the pressure in the sample side of dehumidifier 10 or 100 may be sub-atmospheric, or a vacuum, in another aspect of the invention, the pressure on the sample side of dehumidifier 10 or 110 may be super atmospheric, for example, a pressure or pressure differential of 1 psig or greater, for instance 10 psi or greater. One limit on the pressure that may be applied to the sample side of dehumidifier 10 or 110 may be the strength of the membrane used. However, a membrane may be provided having sufficient strength and supported by an appropriate support structure to prevent collapse or damage of the membrane such that greater pressures, for example, pressures or pressure differentials of 20 psig or greater, may be provided on the sample side of dehumidifier 10 or 110.

FIGS. 12A, 12B, and 12C are schematic views of further flow path cross sections according to further aspects of the invention. FIG. 12A is a schematic cross sectional view of a dehumidifier 300 having a flow passage having a generally arcuate or bent rectangle shape according to one aspect of the invention. Dehumidifier 300 includes at least one membrane 302, typically, two membranes 302, mounted on support structures 304 and 306. Support structures 304 and 306 may have the construction of support structure 34 shown in FIGS. 5 and 6; however, support structures 304 and 306 are radiused as shown in FIG. 12 A. Support structures 304 and 306 provide support wherein membranes 302 also provide a radiused profile and define a flow path 308 having radiused boundaries defined by membranes 302. Similar to support structure 34, support structures 304 and 306 may typically include flow passages, for example, serpentine flow passages, for passing a purge gas. As in the aspect of the invention shown in FIG. 4, support structures 304 and 306 may be mounted in a housing 310, shown in cross-section in FIG. 12A. Housing 310 may comprise two or more sub housings to facilitate assembly and servicing of dehumidifier 310, for example, end plates similar to end plate 22 and 24 of dehumidifier 10. The materials, hardware, and mode of assembly and operation of humidifier 300 may be similar to humidifier 10 shown in FIGS. 1-4.

FIG. 12B is a schematic cross sectional view of a dehumidifier 400 having a flow passage having a generally eye-shaped cross section, that is, having a generally varying width between the boundaries of the flow passage, according to another aspect of the invention. Dehumidifier 400 includes at least one membrane 402, typically, two membranes 402, mounted on support structures 404 and 406. Support structures 404 and 406 may have the construction of support structure 34 shown in FIGS. 5 and 6; however, support structures 404 and 406 are radiused as shown in FIG. 12B. Support structures 404 and 406 provide support wherein membranes 402 also provide a radiused profile and define a flow path 408 having radiused boundaries defined by membranes 402. Similar to support structure 34, support structures 404 and 406 may typically include flow passages, for example, serpentine flow passages, for passing a purge gas. As in the aspect of the invention shown in FIG. 4, support structures 404 and 406 may be mounted in a housing 410, shown in cross-section in FIG. 12A. Housing 410 may comprise two or more sub housings to facilitate assembly and servicing of dehumidifier 410, for example, end plates similar to end plate 22 and 24 of dehumidifier 10. The materials, hardware, and mode of assembly and operation of humidifier 400 may be similar to humidifier 10 shown in FIGS. 1-4.

FIG. 12C is a schematic cross sectional view of a dehumidifier 500 having a flow passage having a generally crescent-shaped cross section according to another aspect of the invention. Dehumidifier 500 includes at least one membrane 502, typically, two membranes 502, mounted on support structures 504 and 506. Support structures 504 and 506 may also have the construction of support structure 34 shown in FIGS. 5 and 6; however, support structures 504 and 506 are radiused as shown in FIG. 12C. Support structures 504 and 506 provide support wherein membranes 502 also provide a radiused profile and define a flow path 508 having radiused boundaries defined by membranes 502. Similar to support structure 34, support structures 504 and 506 may typically include flow passages, for example, serpentine flow passages, for passing a purge gas. As in the aspect of the invention shown in FIG. 4, support structures 504 and 506 may be mounted in a housing 510, shown in cross-section in FIG. 12C. Housing 510 may comprise two or more sub housings to facilitate assembly and servicing of dehumidifier 510, for example, end plates similar to end plate 22 and 24 of dehumidifier 10. The materials, hardware, and mode of assembly and operation of humidifier 500 may be similar to humidifier 10 shown in FIGS. 1-4.

While several aspects of the present invention have been described and depicted herein, alternative aspects may be effected by those skilled in the art to accomplish the same objectives. Accordingly, it is intended by the appended claims to cover all such alternative aspects as fall within the true spirit and scope of the invention.

The invention claimed is:

1. A membrane diffusion gas dehumidifier adapted to dehumidify particle-containing gas streams while minimizing loss of particles from the gas streams, the dehumidifier comprising:

an inlet for the gas having a first moisture content;

a treatment zone comprising a flow path having a first boundary elongated in a direction substantially perpendicular to a direction of flow of the gas, a second boundary opposite the first boundary and elongated in a direction substantially perpendicular to the direction of flow of the gas, and a width comprising the distance between the first boundary and the second boundary, wherein at least one of the first boundary and the second boundary of the flow path comprises a water-permeable membrane, the membrane having a first side exposed to the treatment zone and a second side opposite the first side;

a transitional flow path between the inlet and the treatment zone, the transitional flow path adapted to minimize obstruction and loss of particles during transfer through the transitional flow path;

means for exposing the second side of the membrane to a treatment gas having a second moisture content, lower than the first moisture content, wherein at least some moisture passes from the gas through the membrane to the treatment gas; and a dehumidified gas outlet.

2. The dehumidifier as recited in claim 1, further comprising at least one support structure adapted to support the membrane.

3. The dehumidifier as recited in claim 2, wherein the support structure provides a flow path for the treatment gas.

4. The dehumidifier as recited in claim 3, wherein the flow path for the treatment gas is adapted to minimize the formation of a boundary layer on the second side of the membrane.

5. The dehumidifier as recited in claim 3, wherein the flow path for the treatment gas is adapted to provide a turbulent flow of treatment gas.

6. The dehumidifier as recited in claim 1, wherein the inlet gas comprises a gas having a first vapor pressure and wherein the means for exposing the second side of the membrane to a treatment gas further comprises means for providing a treatment gas having a second vapor pressure, lower than the first vapor pressure.

7. The dehumidifier as recited in claim 1, wherein the treatment zone flow path comprises a rectangular cross section in the direction of flow.

8. The dehumidifier as recited in claim 1, wherein the inlet comprises a circular cross section having a diameter, and wherein the width of the treatment zone is less than the diameter.

9. The dehumidifier as recited in claim 7, wherein the rectangular cross section comprises a length greater than the width.

10. The dehumidifier as recited in claim 7, wherein the rectangular cross section of the flow path comprises an aspect ratio of at least about 5 to 1.

11. The dehumidifier as recited in claim 3, wherein the support structure comprises a plate and a plurality of ribs projecting from the plate, the ribs supporting the membrane and defining the flow path for the treatment gas.

12. The dehumidifier as recited in claim 1, wherein the at least one water-permeable membrane comprises a perfluorosulfonic acid polymer.

13. A method of dehumidifying a particle-containing gas stream while minimizing loss of particles from the gas stream, the method comprising:

providing a diffusion gas dehumidifier comprising:

a gas inlet;

a treatment zone comprising a flow path having a first boundary, a second boundary opposite the first boundary, and a width comprising the distance between the first boundary and the second boundary, wherein at least one of the first boundary and the second boundary of the flow path comprises a water-permeable membrane, the membrane having a first side exposed to the treatment zone and a second side opposite the first side;

a transitional flow path between the gas inlet and the treatment zone, the transitional flow path adapted to minimize obstruction and loss of particles during transfer through the transitional flow path; and an outlet;

introducing an untreated particle-containing gas stream having a first water vapor content to the gas inlet;

passing the untreated particle-containing gas stream from the gas inlet through the transitional flow path to the treatment zone while minimizing the obstruction and loss of particles;

passing the untreated particle-containing gas stream through the treatment zone;

passing a treatment gas stream passed the second side of the membrane, the treatment gas stream having a second water vapor content less than the first water vapor content, whereby at least some water vapor in the untreated gas stream passes through the membrane to the treatment gas stream to provide a dehumidified particle-containing gas stream; and discharging the dehumidified particle-containing gas stream from the outlet.

14. The method as recited in claim 13, wherein the method is practiced wherein the dehumidified gas stream discharged from the outlet includes at least 80% of the particulate matter introduced at the inlet.

15. The method as recited in claim 13, wherein the untreated gas stream comprises a first pressure, and wherein the treatment gas stream comprises a second pressure less than the first pressure.

16. The method as recited in claim 13, wherein the method further comprises expanding the dehumidified gas stream to provide an expanded dehumidified gas stream, and providing the expanded dehumidified gas stream as the treatment gas stream.

17. The method as recited in claim 13, wherein passing the untreated gas stream through the treatment zone comprises passing the untreated gas stream in a first direction, and wherein introducing a treatment gas stream to the second side of the membrane comprises passing the treatment gas stream in a second direction, opposite the first direction.

18. The method as recited in claim 13, wherein passing a treatment gas stream passed the second side of the membrane comprises passing the treatment gas stream as a turbulent flow whereby formation of a boundary layer on the second side of the membrane is minimized.

19. A particulate matter sampling system for a gas, the system comprising:

a diffusion gas dehumidifier comprising:

a gas inlet;

a treatment zone comprising a flow path having a first boundary, a second boundary opposite the first boundary, and a width comprising the distance between the first boundary and the second boundary, wherein at least one of the first boundary and the second boundary of the flow path comprises a water-permeable membrane, the membrane having a first side exposed to the treatment zone and a second side opposite the first side;

at least one vacuum inlet;

a least one vacuum outlet; and a dehumidified gas outlet;

a particulate matter measuring device having an inlet in fluid communication with the dehumidifier gas outlet and an outlet;

a flow controller having an inlet in fluid communication with the particulate matter measuring device outlet and an outlet in fluid communication with the at least one dehumidifier vacuum inlet; and a source of vacuum operatively connected to the at least one dehumidifier vacuum outlet.

20. The system as recited in claim 19, wherein the source of vacuum is adapted to draw an untreated gas into the dehumidifier gas inlet.

21. The system as recited in claim 19, further comprising a size selective gas inlet having an outlet in fluid communication with the untreated gas inlet.

22. A method of treating a particle-containing gas stream while minimizing loss of particles from the gas stream, the method comprising:

providing a dehumidifying device having water vapor permeable membrane, the membrane having a sample side and a purge side opposite the sample side;

passing the particle-containing gas stream having a first water vapor concentration passed the sample side of the membrane;

turbulently passing a treatment gas stream having a second water vapor concentration lower than the first water vapor concentration passed the purge side of the membrane;

passing at least some water vapor from the particle-containing gas stream through the membrane to produce a dehumidified particle-containing gas stream having a third water vapor concentration lower than the first water vapor concentration while minimizing loss of particles from the particle-containing gas stream; and returning the dehumidified gas stream as the treatment gas stream in the dehumidifying device.

23. The method as recited in claim 22, further comprising, expanding the dehumidified gas stream to produce an expanded and dehumidified gas stream having a fourth water vapor concentration, lower than the third water vapor concentration.

24. The method as recited in claim 21, wherein passing the gas stream passed the sample side of the membrane is practiced with the use of a source of vacuum.

25. The method as recited in claim 22, wherein the method is practiced wherein the dehumidified particle-containing gas stream contains at least about 80% of the particles in the particle-containing gas stream.

26. A membrane support structure adapted to provide at least one flow passage for transmitting a treatment fluid past a membrane, the support structure comprising:

a plate having a surface; and a plurality of ribs mounted to the plate, the plurality of ribs adapted to support the membrane;

wherein, when the membrane is mounted to the support structure, the membrane, the plurality of ribs, and the surface of the plate define boundaries of the at least one flow passage, and the at least one flow passage comprises a cross section sized to at least one of:

(a) maximize at least one of treatment fluid flow velocity and treatment fluid flow turbulence for a given treatment fluid flow rate and (b) minimize development of a boundary layer on the membrane for a given treatment fluid flow rate.

27. The support structure as recited in claim 26, wherein the at least one passage is sized to provide a treatment fluid flow velocity of at least 15 meters per second.

28. The support structure as recited in claim 27, wherein the at least one flow passage comprises a serpentine flow path.

29. The dehumidifier as recited in claim 1, wherein at least one of the first boundary and the second boundary is a radiused boundary.

30. The dehumidifier as recited in claim 1, wherein the width varies.

31. The method as recited in claim 13, wherein at least one of the first boundary and the second boundary is a radiused boundary.

32. The method as recited in claim 13, wherein the width varies.

33. The dehumidifier as recited in claim 1, wherein the transitional flow path includes a recess which minimizes particulate loss through surface contact of particulate matter in the gas.

34. The dehumidifier as recited in claim 33, wherein the recess comprises at least one of (a) a curvilinear surface and (b) a pair of inclined linear surfaces.

35. The system as recited in claim 19, wherein the diffusion gas humidifier further comprises a transition flow path providing a low particulate loss gradual transition from a circular gas inlet cross section to an elongated treatment zone cross section.

36. The system as recited in claim 35, wherein the transition flow path includes a recess to minimize particulate loss through surface contact of particulate matter in the gas.

37. The support structure as recited in claim 26, wherein the at least one flow passage comprises a serpentine flow path.

38. The support structure as recited in claim 26, wherein the treatment fluid comprises a gaseous treatment fluid.

39. The support structure as recited in claim 38, wherein the gaseous treatment fluid comprises a gas having a low moisture content.

40. The support structure as recited in claim 26, wherein the treatment fluid comprises a dehumidifying treatment fluid.

41. The support structure as recited in claim 26, wherein the plurality of ribs mounted to the plate comprise a plurality of ribs projecting from the plate.

42. The support structure as recited in claim 26, wherein the plurality of ribs mounted to the plate comprise a plurality of substantially parallel ribs.

43. The support structure as recited in claim 26, wherein the plate comprises at least one hole for passing the treatment fluid.

44. The support structure as recited in claim 26, wherein the at least one flow passage comprises a plurality of flow passages and wherein the plate comprises a plurality of relief grooves adapted to permit passage of treatment gas between at least two of the plurality of flow passages.

* * * * *